US010682229B2

(12) United States Patent
Guidotti et al.

(10) Patent No.: US 10,682,229 B2
(45) Date of Patent: Jun. 16, 2020

(54) POST-IMPLANTATION TENSIONING IN CARDIAC IMPLANTS

(71) Applicant: 4Tech Inc., Waltham, MA (US)

(72) Inventors: Andrea Guidotti, Zurich (CH); Idan Tobis, Beth Hashmonai (IL); Kevin Lynn, Athenry (IE); Chris Moran, Claremorris (IE); Michael Gilmore, Ardrahan (IE)

(73) Assignee: 4Tech Inc., Waltham, MA (US)

( * ) Notice: Subject to any disclaimer, the term of this patent is extended or adjusted under 35 U.S.C. 154(b) by 263 days.

(21) Appl. No.: 15/891,664

(22) Filed: Feb. 8, 2018

(65) Prior Publication Data

US 2018/0221148 A1    Aug. 9, 2018

Related U.S. Application Data

(60) Provisional application No. 62/456,202, filed on Feb. 8, 2017.

(51) Int. Cl.
  *A61F 2/24*    (2006.01)
  *A61B 17/04*   (2006.01)
  (Continued)

(52) U.S. Cl.
  CPC ........ *A61F 2/2442* (2013.01); *A61B 17/0401* (2013.01); *A61F 2/2427* (2013.01);
  (Continued)

(58) Field of Classification Search
  CPC ............... A61F 2002/249; A61F 2/2466; A61F 2/2442; A61F 2/2487; A61F 2017/0409;
  (Continued)

(56) References Cited

U.S. PATENT DOCUMENTS 4,602,911 A    7/1986 Ahmadi et al.
5,474,518 A    12/1995 Farrer Velazquez
(Continued)

FOREIGN PATENT DOCUMENTS

WO   2006097931 A2   9/2006
WO   2006111391 A1   10/2006
(Continued)

OTHER PUBLICATIONS

JPO, Office Action dated Mar. 27, 2018, Japanese Patent Application No. 098926/2017 (English translation).
(Continued)

*Primary Examiner* — Christopher L Templeton
(74) *Attorney, Agent, or Firm* — UltimatEdge IP Law Group, P.C.; Dean G. Stathakis; Vito A. Canusco, III

(57) ABSTRACT

A method of treating a heart of a patient is provided. The method includes implanting a first tissue anchor in cardiac tissue of the patient and a second tissue anchor in the patient, such that the first and the second tissue anchors are coupled together by one or more tethers. Thereafter, after allowing at least 24 hours for tissue growth on the first tissue anchor to strengthen anchoring of the first tissue anchor in the cardiac tissue, tension is applied between the first and the second tissue anchors using at least a longitudinal portion of the one or more tethers. Other embodiments are also described.

13 Claims, 21 Drawing Sheets

(51) Int. Cl.
*A61B 17/00* (2006.01)
*A61F 2/30* (2006.01)
*A61F 2/915* (2013.01)

(52) U.S. Cl.
CPC .. *A61F 2/2466* (2013.01); *A61B 2017/00243* (2013.01); *A61B 2017/00783* (2013.01); *A61B 2017/0409* (2013.01); *A61B 2017/0441* (2013.01); *A61B 2017/0464* (2013.01); *A61B 2017/0488* (2013.01); *A61B 2017/0496* (2013.01); *A61F 2/2451* (2013.01); *A61F 2/2463* (2013.01); *A61F 2/2487* (2013.01); *A61F 2/915* (2013.01); *A61F 2002/30477* (2013.01)

(58) Field of Classification Search
CPC ...... A61F 2017/00783; A61F 17/00234; A61F 17/0401
See application file for complete search history.

(56) References Cited

U.S. PATENT DOCUMENTS

| | | | |
|---|---|---|---|
| 6,629,534 | B1 | 10/2003 | St. Goar et al. |
| 6,723,038 | B1 | 4/2004 | Schroeder et al. |
| 7,335,213 | B1 | 2/2008 | Hyde et al. |
| 8,029,518 | B2 | 10/2011 | Goldfarb et al. |
| 8,382,829 | B1 | 2/2013 | Call et al. |
| 8,475,525 | B2 | 7/2013 | Maisano et al. |
| 8,808,368 | B2 | 8/2014 | Maisano et al. |
| 9,241,702 | B2 | 1/2016 | Maisano et al. |
| 9,307,980 | B2 | 4/2016 | Gilmore et al. |
| 9,636,224 | B2 | 5/2017 | Zipory et al. |
| 2003/0105519 | A1 | 6/2003 | Fasol et al. |
| 2003/0233142 | A1 | 12/2003 | Morales et al. |
| 2004/0039443 | A1 | 2/2004 | Solem et al. |
| 2004/0186566 | A1 | 9/2004 | Hindrichs et al. |
| 2004/0225304 | A1 | 11/2004 | Vidlund et al. |
| 2004/0243229 | A1 | 12/2004 | Vidlund et al. |
| 2004/0260317 | A1 | 12/2004 | Bloom et al. |
| 2005/0070999 | A1 | 3/2005 | Spence |
| 2005/0177180 | A1 | 8/2005 | Kaganov |
| 2005/0222488 | A1 | 10/2005 | Chang et al. |
| 2006/0030885 | A1 | 2/2006 | Hyde |
| 2006/0058842 | A1 | 3/2006 | Wilke et al. |
| 2006/0106278 | A1 | 5/2006 | Machold et al. |
| 2006/0241745 | A1 | 10/2006 | Solem |
| 2006/0276890 | A1 | 12/2006 | Solem et al. |
| 2006/0282161 | A1 | 12/2006 | Huyn et al. |
| 2007/0049942 | A1 | 3/2007 | Hindrichs et al. |
| 2007/0118151 | A1 | 5/2007 | Davidson |
| 2007/0270943 | A1 | 11/2007 | Solem et al. |
| 2007/0282429 | A1 | 12/2007 | Hauser et al. |
| 2008/0027483 | A1 | 1/2008 | Cartledge |
| 2009/0177274 | A1 | 7/2009 | Scorsin et al. |
| 2009/0259260 | A1 | 10/2009 | Bentley et al. |
| 2010/0023117 | A1 | 1/2010 | Yoganathan |
| 2011/0011917 | A1 | 1/2011 | Loulmet |
| 2011/0029071 | A1 | 2/2011 | Zlotnick et al. |
| 2011/0184510 | A1 | 7/2011 | Maisano et al. |
| 2011/0288635 | A1 | 11/2011 | Miller et al. |
| 2012/0035712 | A1 | 2/2012 | Maisano et al. |
| 2012/0296417 | A1* | 11/2012 | Hill ........................ A61F 2/2445 623/2.11 |
| 2013/0018459 | A1* | 1/2013 | Maisano ............ A61B 17/0401 623/2.37 |
| 2013/0023985 | A1 | 1/2013 | Khairkhahan et al. |
| 2013/0030522 | A1 | 1/2013 | Rowe et al. |
| 2013/0046380 | A1* | 2/2013 | Maisano ................ A61F 2/2457 623/2.36 |
| 2013/0079873 | A1 | 3/2013 | Migliazza et al. |
| 2013/0096672 | A1 | 4/2013 | Reich |
| 2013/0325115 | A1 | 12/2013 | Maisano et al. |
| 2014/0114390 | A1 | 4/2014 | Tobis et al. |
| 2014/0324164 | A1 | 10/2014 | Gross et al. |
| 2015/0119936 | A1 | 4/2015 | Gilmore et al. |
| 2015/0223934 | A1 | 8/2015 | Vidlund et al. |
| 2016/0022488 | A1* | 1/2016 | Dimmig .................. A61F 9/007 606/107 |
| 2016/0158008 | A1 | 6/2016 | Miller et al. |
| 2016/0242762 | A1 | 8/2016 | Gilmore et al. |
| 2016/0374689 | A1* | 12/2016 | Tanaka ............. A61B 17/12104 606/191 |
| 2017/0056174 | A1 | 3/2017 | Tobis et al. |
| 2018/0036119 | A1 | 2/2018 | Wei et al. |
| 2018/0289478 | A1 | 10/2018 | Quill |
| 2018/0318071 | A1 | 11/2018 | Lozonschi et al. |

FOREIGN PATENT DOCUMENTS

| | | | |
|---|---|---|---|
| WO | 2007103562 | A2 | 9/2007 |
| WO | 2011089601 | A1 | 7/2011 |
| WO | 2014141239 | A1 | 9/2014 |
| WO | 2015006729 | A2 | 1/2015 |
| WO | 2015063580 | A2 | 5/2015 |
| WO | 2018148324 | A1 | 8/2018 |

OTHER PUBLICATIONS

USPTO, Office Action dated Oct. 24, 2017, U.S. Appl. No. 15/365,495.
USPTO, Office Action dated Apr. 12, 2018, U.S. Appl. No. 15/365,495.
WIPO, Invitation to pay additional fees dated May 4, 2018, International Patent Application Serial No. PCT/US2018/017352.
WIPO, International Search Report and a Written Opinion both dated May 28, 2018, International Patent Application Serial No. PCT/US2018/019420.
WIPO, International Search Report and a Written Opinion both dated Aug. 28, 2018, International Patent Application Serial No. PCT/US2018/017352.
WIPO, PCT Form ISA210, International Search Report dated Apr. 30, 2019, International Patent Application Serial No. PCT/US2018/045523, pp. 3.
WIPO, PCT Form ISA237, Written Opinion both dated Apr. 30, 2019, International Patent Application Serial No. PCT/US2018/045523, pp. 7.
USPTO, Jul. 26, 2018 Office Action for U.S. Appl. No. 15/365,495.
USPTO, Mar. 21, 2019 Office Action for U.S. Appl. No. 15/903,619.

* cited by examiner

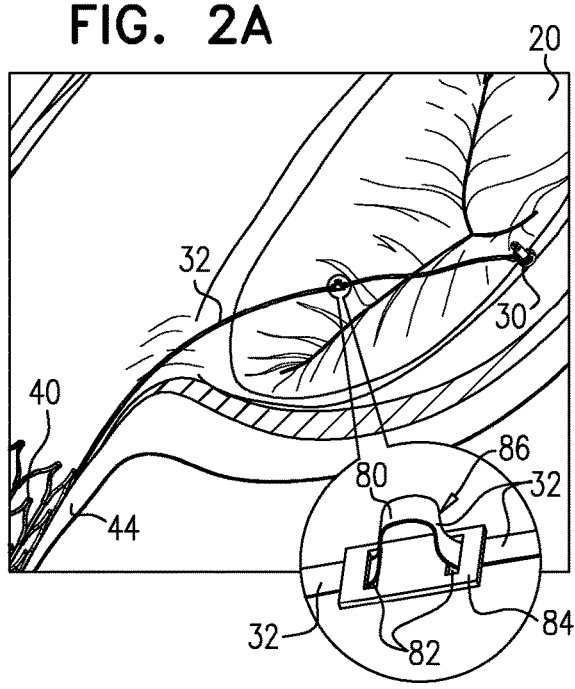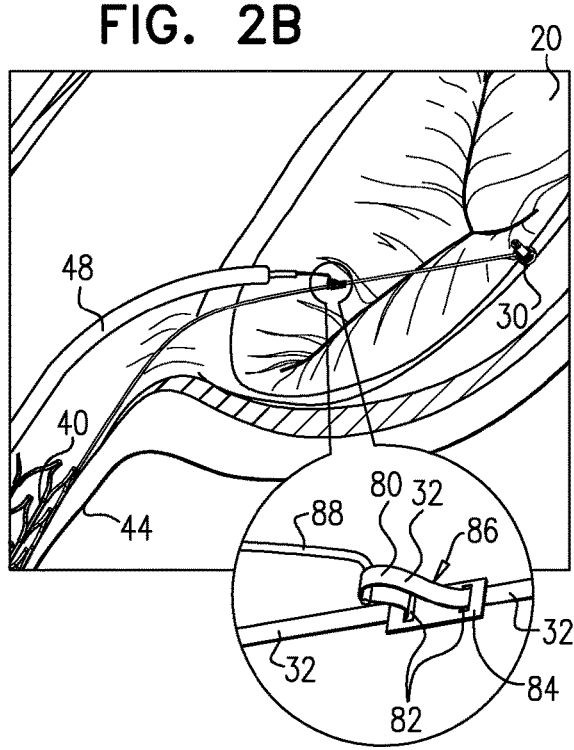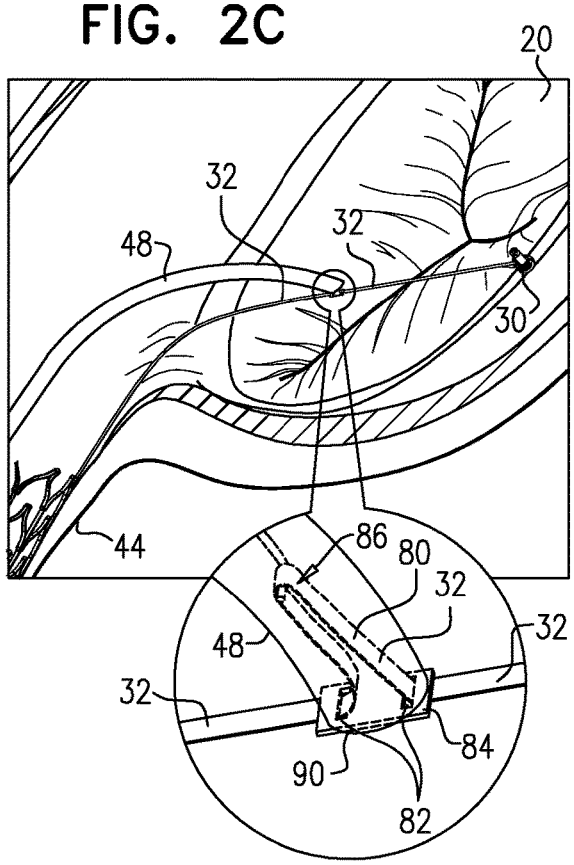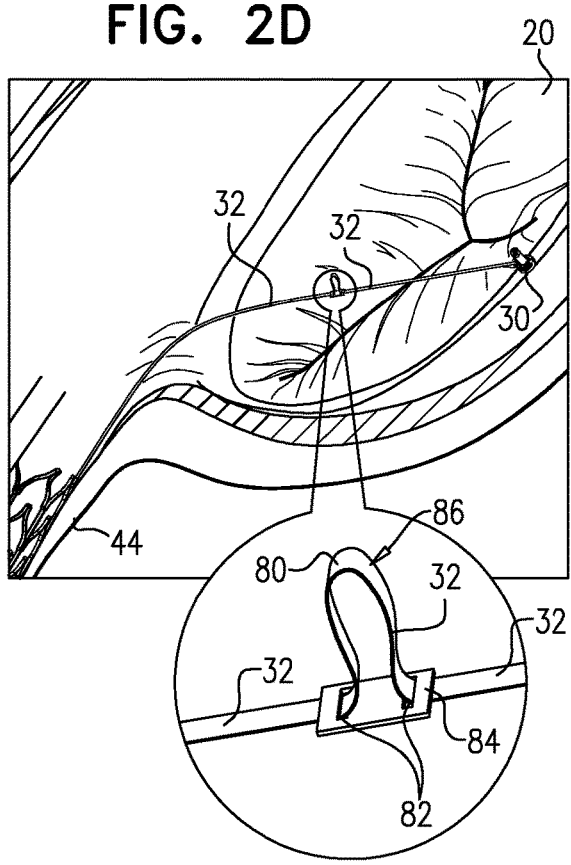

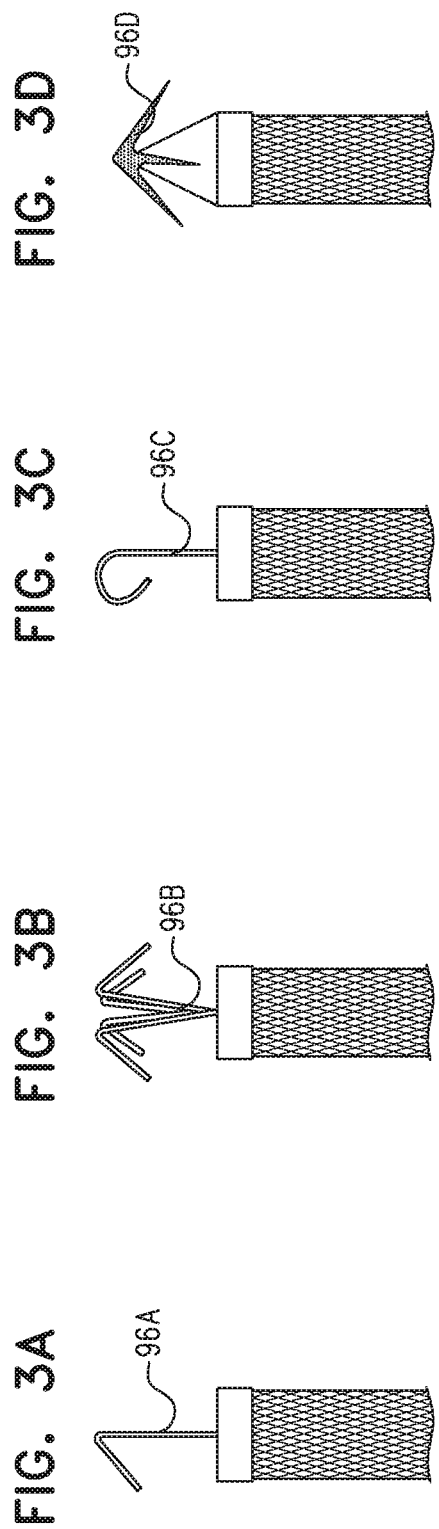

POST-IMPLANTATION TENSIONING IN CARDIAC IMPLANTS

CROSS-REFERENCE TO RELATED APPLICATIONS

The present application claims the benefit of U.S. Provisional Application 62/456,202, filed Feb. 8, 2017, which is assigned to the assignee of the present application and is incorporated herein by reference. The present application is related to International Application PCT/US2018/017352, filed Feb. 8, 2018, entitled, "Post-implantation tensioning in cardiac implants."

FIELD OF THE APPLICATION

The present invention relates generally to minimally-invasive valve repair, and more specifically to minimally-invasive methods for repairing the tricuspid valve.

BACKGROUND OF THE APPLICATION

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical.

U.S. Pat. No. 8,475,525 to Maisano et al. describes a method that includes implanting at least a first tissue-engaging element in a first portion of tissue in a vicinity of a heart valve of a patient, implanting at least a second tissue-engaging element in a portion of a blood vessel that is in contact with an atrium of a heart of the patient, and drawing at least a first leaflet of the valve toward at least a second leaflet of the valve by adjusting a distance between the portion of the blood vessel and the first portion of tissue in the vicinity of the heart valve of the patient. In one configuration, a proximal end portion of a longitudinal member is shaped so as to define one or more engaging elements (e.g., hooks or barbs), which are coupleable with the struts of a stent member in order to maintain the tension applied to a longitudinal member for remodeling the tricuspid valve.

SUMMARY OF THE APPLICATION

Some applications of the present invention provide a method of treating a heart of a patient, such as to reduce tricuspid valve regurgitation. The method includes implanting a first tissue anchor in cardiac tissue of the patient and a second tissue anchor in the patient, such that the first and the second tissue anchors are coupled together by one or more tethers. Thereafter, after allowing at least 24 hours for tissue growth on the first tissue anchor to strengthen anchoring of the first tissue anchor in the cardiac tissue, tension is applied between the first and the second tissue anchors using at least a longitudinal portion of the one or more tethers. Typically, the one or more tethers are slack before the tension is applied.

Other applications of the present invention provide another method of treating a heart of a patient, including implanting a first tissue anchor in cardiac tissue of the patient. Thereafter, after allowing at least 24 hours for tissue growth on the first tissue anchor to strengthen anchoring of the first tissue anchor in the cardiac tissue, a second tissue anchor is implanted in the patient, the first and the second tissue anchors are coupled together using one or more tethers, and tension is applied between the first and the second tissue anchors using the one or more tethers.

There is therefore provided, in accordance with an application of the present invention, a method of treating a heart of a patient, including:

implanting a first tissue anchor in cardiac tissue of the patient and a second tissue anchor in the patient, such that the first and the second tissue anchors are coupled together by one or more tethers;

thereafter, after allowing at least 24 hours for tissue growth on the first tissue anchor to strengthen anchoring of the first tissue anchor in the cardiac tissue, applying tension between the first and the second tissue anchors using at least a longitudinal portion of the one or more tethers.

For some applications, the one or more tethers are slack before applying the tension.

For some applications, the one or more tethers are one or more first tethers, and applying the tension includes:

coupling a second tether to a coupling site along the one or more first tethers; and applying the tension between the first and the second tissue anchors using the at least a longitudinal portion of the one or more first tethers and the second tether.

For some applications, coupling the second tether to the coupling site includes coupling, to the coupling site, a coupling element that is attached to the second tether.

For some applications, the coupling element includes a hook.

For some applications, applying the tension includes coupling the second tether to the second tissue anchor.

For some applications, the second tissue anchor includes a stent that includes a plurality of struts, and coupling the second tether to the second tissue anchor includes coupling, to one or more of the struts, a coupling element that is attached to the second tether.

For some applications, the coupling element includes a hook.

For some applications, the coupling element is shaped so as to define an opening.

For some applications, at least one of the struts is oriented axially as a backbone, and coupling the coupling element to the one or more of the struts includes coupling the coupling element to the backbone.

For some applications, the backbone is shaped so as to define one or more hooks, and coupling the coupling element to the backbone includes coupling the coupling element to one or more of the hooks.

For some applications, a longitudinal portion of the one or more tethers passes through one or more openings of a locking frame so as to form a tether loop, and applying the tension includes enlarging the tether loop by pulling on the tether loop.

For some applications, the one or more openings are two openings, and the longitudinal portion of the one or more tethers passes through the two openings.

For some applications, applying the tension includes applying the tension after allowing at least one week for tissue growth on the first tissue anchor.

For some applications, applying the tension includes applying the tension within two months after implanting the first tissue anchor.

For some applications, implanting the first tissue anchor includes implanting the first tissue anchor in the vicinity of the tricuspid valve of the patient.

For some applications, implanting the second tissue anchor includes implanting the second tissue anchor in a blood vessel selected from the group consisting of: a superior vena cava (SVC), an inferior vena cava (IVC), and a coronary sinus.

There is further provided, in accordance with an application of the present invention, a system for treating a heart of a patient, including:

a first tissue anchor configured to be implanted in cardiac tissue of the patient;

a second tissue anchor configured to be implanted in the patient;

one or more first tethers that couple together the first and the second tissue anchors; and a second tether configured to be coupled to a coupling site along the one or more first tethers, so as to apply tension between the first and the second tissue anchors using (a) the second tether and (b) a longitudinal portion of the one or more first tethers.

For some applications, the system further includes a coupling element that is attached to the second tether and is configured to be coupled to the coupling site along the one or more first tethers. For some applications, the coupling element includes a hook.

For some applications, the system further includes a coupling element that is attached to the second tether and is configured to be coupled to the second tissue anchor. For some applications, the second tissue anchor includes a stent that includes a plurality of struts, and the coupling element is configured be coupled to one or more of the struts. For some applications, the coupling element includes a hook. For some applications, the coupling element is shaped so as to define an opening. For some applications, at least one of the struts is oriented axially as a backbone, and the coupling element is configured to be coupled to the backbone. For some applications, the backbone is shaped so as to define one or more hooks, and the coupling element is configured to be coupled to one or more of the hooks.

There is further provided, in accordance with an application of the present invention, a system for treating a heart of a patient, including:

a first tissue anchor configured to be implanted in cardiac tissue of the patient;

a second tissue anchor configured to be implanted in the patient;

one or more tethers that couple together the first and the second tissue anchors, wherein a longitudinal portion of the one or more tethers passes through one or more openings of a locking frame so as to form a tether loop, such that enlargement of the tether loop by pulling on the tether loop applies tension between the first and the second tissue anchors using at least a longitudinal portion of the one or more tethers.

For some applications, the one or more openings are two openings, and the longitudinal portion of the one or more tethers passes through the two openings.

There is further provided, in accordance with an application of the present invention, a method of treating a heart of a patient, including:

implanting a first tissue anchor in cardiac tissue of the patient;

thereafter, after allowing at least 24 hours for tissue growth on the first tissue anchor to strengthen anchoring of the first tissue anchor in the cardiac tissue:

implanting a second tissue anchor in the patient;

coupling the first and the second tissue anchors together using one or more tethers; and applying tension between the first and the second tissue anchors using the one or more tethers.

For some applications, coupling the first and the second tissue anchors together includes coupling the first and the second tissue anchors together after implanting the second tissue anchor.

For some applications, coupling the first and the second tissue anchors together includes coupling the first and the second tissue anchors together before implanting the second tissue anchor.

For some applications:

the one or more tethers are one or more first tethers, the method further includes implanting a third tissue anchor in cardiac tissue of the patient, such that the first and the third tissue anchors are coupled together by one or more second tethers, coupling the first and the second tissue anchors together includes coupling the first, the second, and the third tissue anchors together using the one or more first tethers and the one or more second tethers, and applying the tension between the first and the second tissue anchors includes applying the tension between the first, the second, and the third tissue anchors using the one or more first tethers and the one or more second tethers.

For some applications, implanting the third tissue anchor includes implanting the third tissue anchor within three hours of implanting the first tissue anchor.

For some applications:

the one or more first tethers are attached to the second tissue anchor and include a coupling element, and coupling the first, the second, and the third tissue anchors together using the one or more first tethers and the one or more second tethers includes coupling the coupling element to the one or more second tethers.

For some applications, the coupling element includes a hook, and coupling the coupling element to the one or more second tethers includes hooking the hook onto the one or more second tethers.

For some applications:

the first tissue anchor includes a tissue-anchoring element and a first coupling element, the one or more tethers are attached to the second tissue anchor and include a second coupling element, and coupling the first and the second tissue anchors together using the one or more tethers includes coupling the second coupling element to the first coupling element.

For some applications, the first coupling element includes a ball, the second coupling element includes a socket, and coupling the first and the second tissue anchors together includes coupling the socket to the ball.

For some applications, the ball is connected to a head of the first tissue anchor by a rod.

For some applications, coupling the socket to the ball includes transitioning the socket from an open, unlocked state to a closed, locked state around the ball.

For some applications, the first coupling element includes a socket, the second coupling element includes a ball, and coupling the first and the second tissue anchors together includes coupling the ball to the socket.

For some applications, the first coupling element includes a loop, the second coupling element includes a hook, and coupling the first and the second tissue anchors together includes hooking the hook onto the loop.

For some applications, the second coupling element includes a loop, and coupling the first and the second tissue anchors together includes coupling the loop to the first coupling element.

For some applications, the first coupling element includes a hook, and coupling the loop to the first coupling element includes coupling the loop to the hook.

For some applications, the first coupling element is coated with a tissue-growth-inhibiting coating.

For some applications, the tissue-anchoring element is coated with a tissue-growth-enhancing coating.

For some applications, implanting the second tissue anchor includes implanting the second tissue anchor after allowing at least one week for tissue growth on the first anchor.

For some applications, implanting the second tissue anchor includes implanting the second tissue anchor within two months after implanting the first tissue anchor.

For some applications, the first tissue anchor includes a helical tissue-anchoring element.

For some applications, the second tissue anchor includes a stent.

For some applications, implanting the first tissue anchor includes implanting the first tissue anchor in the vicinity of the tricuspid valve.

For some applications, implanting the second tissue anchor includes implanting the second tissue anchor in a blood vessel selected from the group consisting of: a superior vena cava (SVC), an inferior vena cava (IVC), and a coronary sinus.

There is further provided, in accordance with an application of the present invention, a method of reducing tricuspid valve regurgitation of a patient, including:

implanting a first tissue anchor in cardiac tissue of the patient in the vicinity of the tricuspid valve;

thereafter, after allowing at least 24 hours for tissue growth on the first tissue anchor to strengthen anchoring of the first tissue anchor in the cardiac tissue:

implanting a second tissue anchor in the patient;

coupling the first and the second tissue anchors together using one or more tethers; and applying tension between the first and the second tissue anchors using the one or more tethers, so as to reduce the tricuspid valve regurgitation.

For some applications, coupling the first and the second tissue anchors together includes coupling the first and the second tissue anchors together after implanting the second tissue anchor.

For some applications, coupling the first and the second tissue anchors together includes coupling the first and the second tissue anchors together before implanting the second tissue anchor.

For some applications, implanting the second tissue anchor includes implanting the second tissue anchor in a blood vessel selected from the group consisting of: a superior vena cava (SVC), an inferior vena cava (IVC), and a coronary sinus.

For some applications, the second tissue anchor includes a stent.

For some applications:

the first tissue anchor includes a tissue-anchoring element and a first coupling element, the one or more tethers are attached to the second tissue anchor and include a second coupling element, and coupling the first and the second tissue anchors together using the one or more tethers includes coupling the second coupling element to the first coupling element.

For some applications, the first coupling element includes a ball, the second coupling element includes a socket, and coupling the first and the second tissue anchors together includes coupling the socket to the ball.

For some applications, the first coupling element includes a loop, the second coupling element includes a hook, and coupling the first and the second tissue anchors together includes hooking the hook onto the loop.

For some applications, the first coupling element includes a hook, and the second coupling element includes a loop, and coupling the first and the second tissue anchors together includes hooking the hook onto the loop.

There is further provided, in accordance with an application of the present invention, a system for treating a heart of a patient, including:

a first tissue anchor configured to be implanted in cardiac tissue of the patient, the first tissue anchor including (a) a tissue-anchoring element and (b) a first coupling element that includes a loop;

a second tissue anchor configured to be implanted in the patient; and one or more tethers, which are attached to the second tissue anchor and include a second coupling element, which includes a hook, and which is configured to be coupled to the first coupling element by hooking the hook onto the loop.

For some applications, the hook is coated with a tissue-growth-inhibiting coating.

For some applications, the first tissue anchor includes a helical tissue-anchoring element.

There is further provided, in accordance with an application of the present invention, a system for treating a heart of a patient, including:

a first tissue anchor configured to be implanted in cardiac tissue of the patient, the first tissue anchor including (a) a tissue-anchoring element and (b) a first coupling element that includes a ball;

a second tissue anchor configured to be implanted in the patient; and one or more tethers, which are attached to the second tissue anchor and include a second coupling element, which includes a socket, and which is configured to be coupled to the first coupling element by coupling the socket to the ball.

For some applications, the ball is connected to a head of the first tissue anchor by a rod.

For some applications, the ball is coated with a tissue-growth-inhibiting coating.

For some applications, the first tissue anchor includes a helical tissue-anchoring element.

There is further provided, in accordance with an application of the present invention, a system for treating a heart of a patient, including:

first and third tissue anchors configured to be implanted in cardiac tissue of the patient;

a second tissue anchor configured to be implanted in the patient;

one or more first tethers, which are attached to the second tissue anchor and include a coupling element; and one or more second tethers that couple together the first and the third tissue anchors, wherein the coupling element is configured to be coupled to the one or more second tethers, to facilitate applying tension between the first, the second, and the third tissue anchors using the one or more first tethers and the one or more second tethers.

For some applications, the coupling element includes a hook, which is configured to be hooked on the one or more second tethers.

The present invention will be more fully understood from the following detailed description of embodiments thereof, taken together with the drawings, in which:

BRIEF DESCRIPTION OF THE DRAWINGS

FIGS. 2A-D are schematic illustrations of another technique for treating a heart of a patient, in accordance with an application of the present invention;

FIGS. 3A-D are schematic illustrations of coupling elements, in accordance with respective applications of the present invention;

DETAILED DESCRIPTION OF APPLICATIONS

Figure 1A:
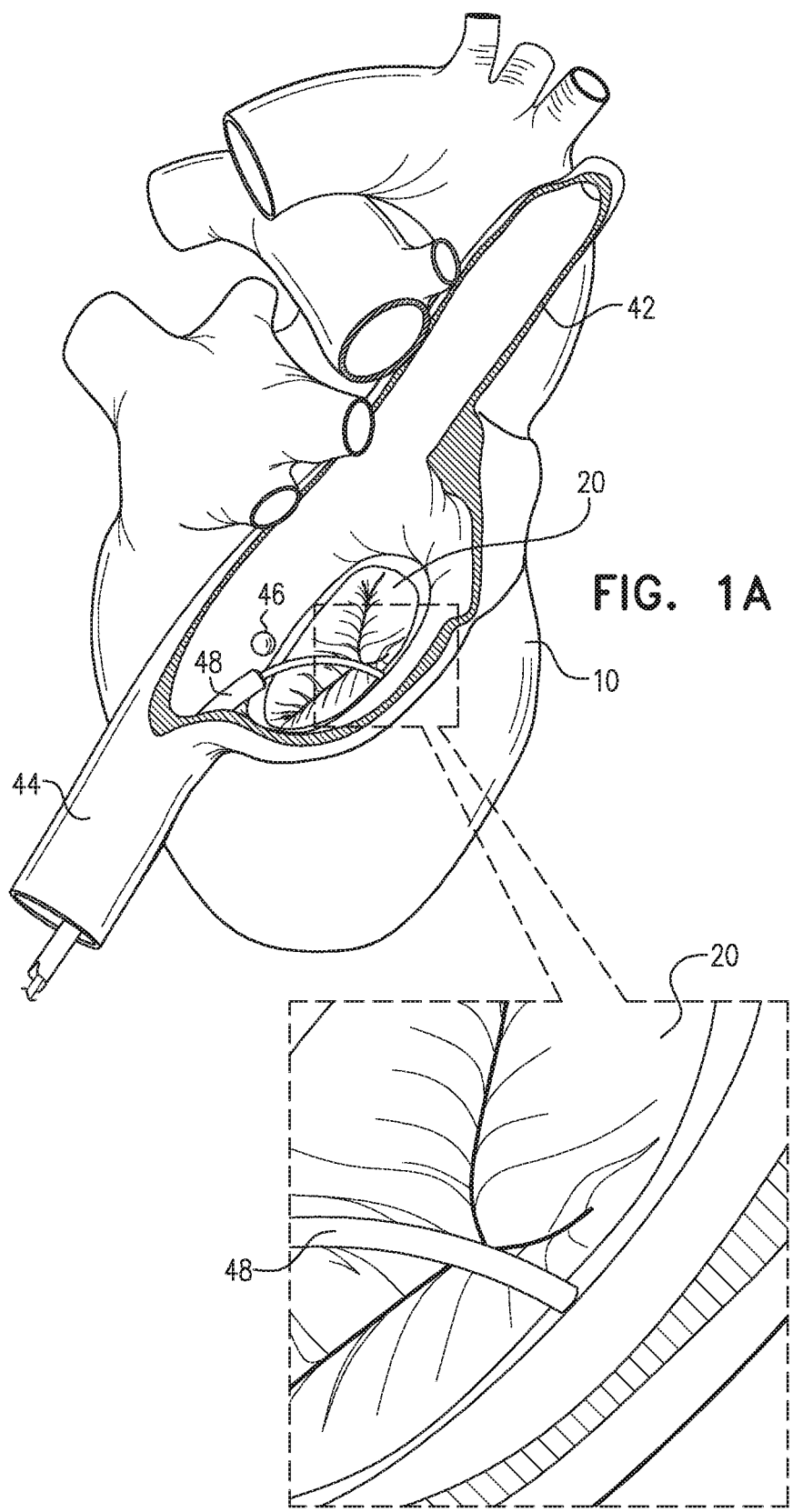
FIGS. 1A-E are schematic illustrations of a technique of treating a heart of a patient, in accordance with an application of the present invention.
Figure 1B:
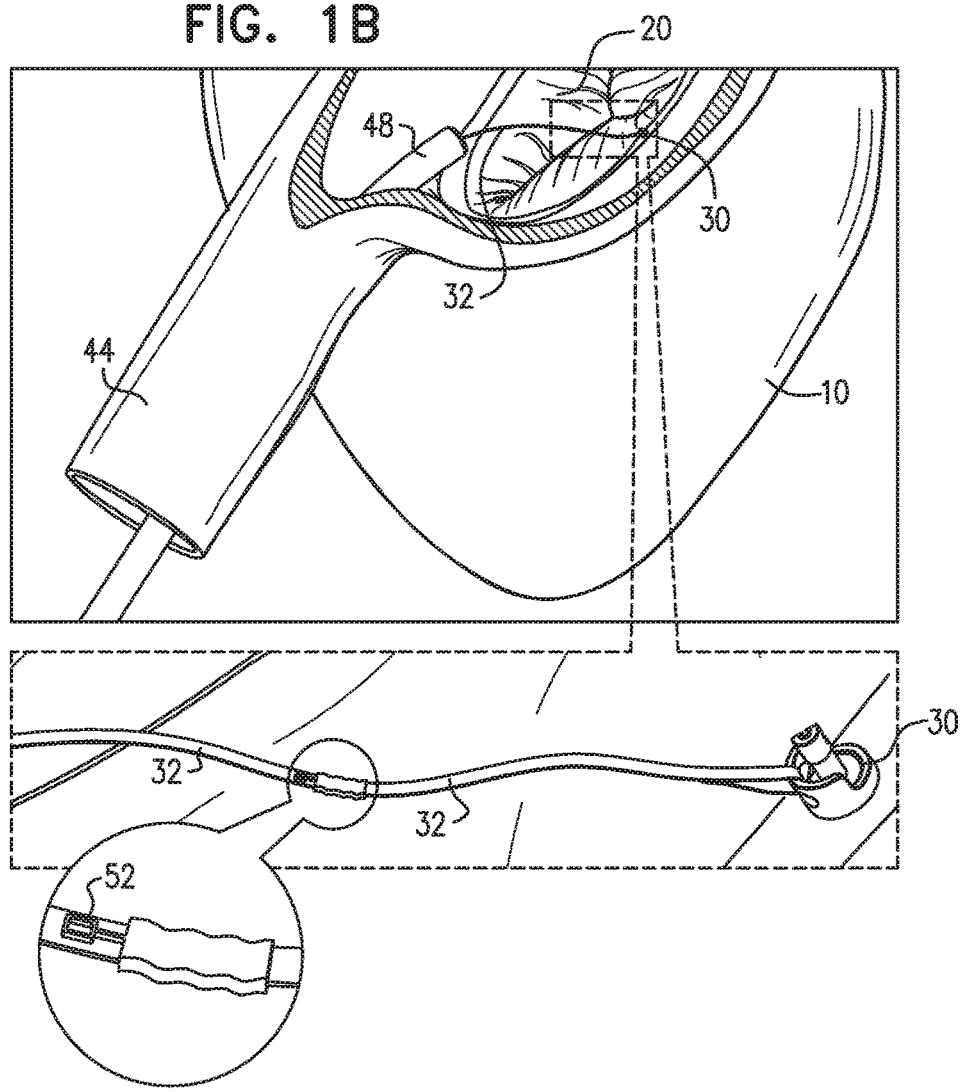
Figure 1C:
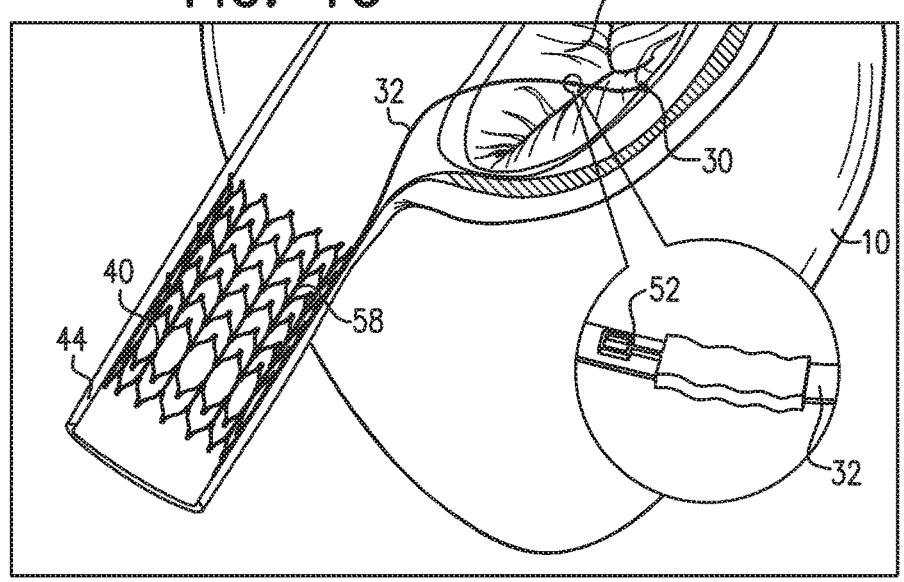

FIGS. 1A-E are schematic illustrations of a technique for treating a heart 10 of a patient, in accordance with an application of the present invention. FIGS. 2A-D are schematic illustrations of another technique for treating a heart 10 of a patient, in accordance with an application of the present invention. For some applications, the techniques of FIGS. 1A-E and 2A-D are used to treat a tricuspid valve 20, such as by reducing tricuspid valve regurgitation.

As shown in FIGS. 1A-C and 2A, during a first stage of an implantation procedure, a first tissue anchor 30 is implanted in cardiac tissue of the patient, and a second tissue anchor 40 is implanted in the patient, either before or after implanting first tissue anchor 30, such that first and second tissue anchors 30 and 40 are coupled together by one or more tethers 32. For example, first tissue anchor 30 may be implanted in the vicinity of tricuspid valve 20 (as shown), e.g., on or near the annulus, and/or second tissue anchor 40 may be implanted in a superior vena cava (SVC) 42, an inferior vena cava (IVC) 44 (as shown), or a coronary sinus 46. Typically, first and second tissue anchors 30 and 40 are implanted in a transcatheter procedure (typically endovascularly, such as percutaneously), via one or more catheters 48, such as described in the applications incorporated hereinbelow by reference. Optionally, the one or more tethers 32 comprise two tethers 32 that are coupled together in situ during the first stage of the implantation procedure, such as using techniques described in one or more of the applications incorporated by reference hereinbelow. For some applications, first tissue anchor 30 comprises a helical tissue-anchoring element, or one of the anchors described in PCT Publications WO 2016/087934 and/or WO 2016/18939, which are incorporated herein by reference.

For some applications, at this first stage of the implantation procedure, the one or more tethers 32 are slack, i.e., do not apply tension between first and second tissue anchors 30 and 40.

As shown in FIGS. 1D-E and 2B-D, thereafter, during a second stage of the implantation procedure, typically after allowing at least 24 hours (e.g., at least one week, such as at least one month) for tissue growth (e.g., fibrous and/or endothelial tissue growth) on first tissue anchor 30 to strengthen anchoring of first tissue anchor 30 in the cardiac tissue, tension is applied between first and second tissue anchors 30 and 40 using at least a longitudinal portion of the one or more tethers 32. For some applications, the tension is applied within two months after implanting first tissue anchor 30. Typically, application of the tension remodels tricuspid valve 20, by drawing two or three of the leaflets together to enhance coaptation.

For some applications, such as shown in FIGS. 1A-E, the one or more tethers 32 are one or more first tethers 32, and applying the tension comprises (a) coupling a second tether 50 to a coupling site 52 along the one or more first tethers 32, and (b) applying the tension between the first and the second tissue anchors 30 and 40 using at least a longitudinal portion 54 (labeled in FIG. 1D) of the one or more first tethers 32 and second tether 50. Typically, longitudinal portion 54 extends from coupling site 52 to first tissue anchor 30.

Figure 1D:
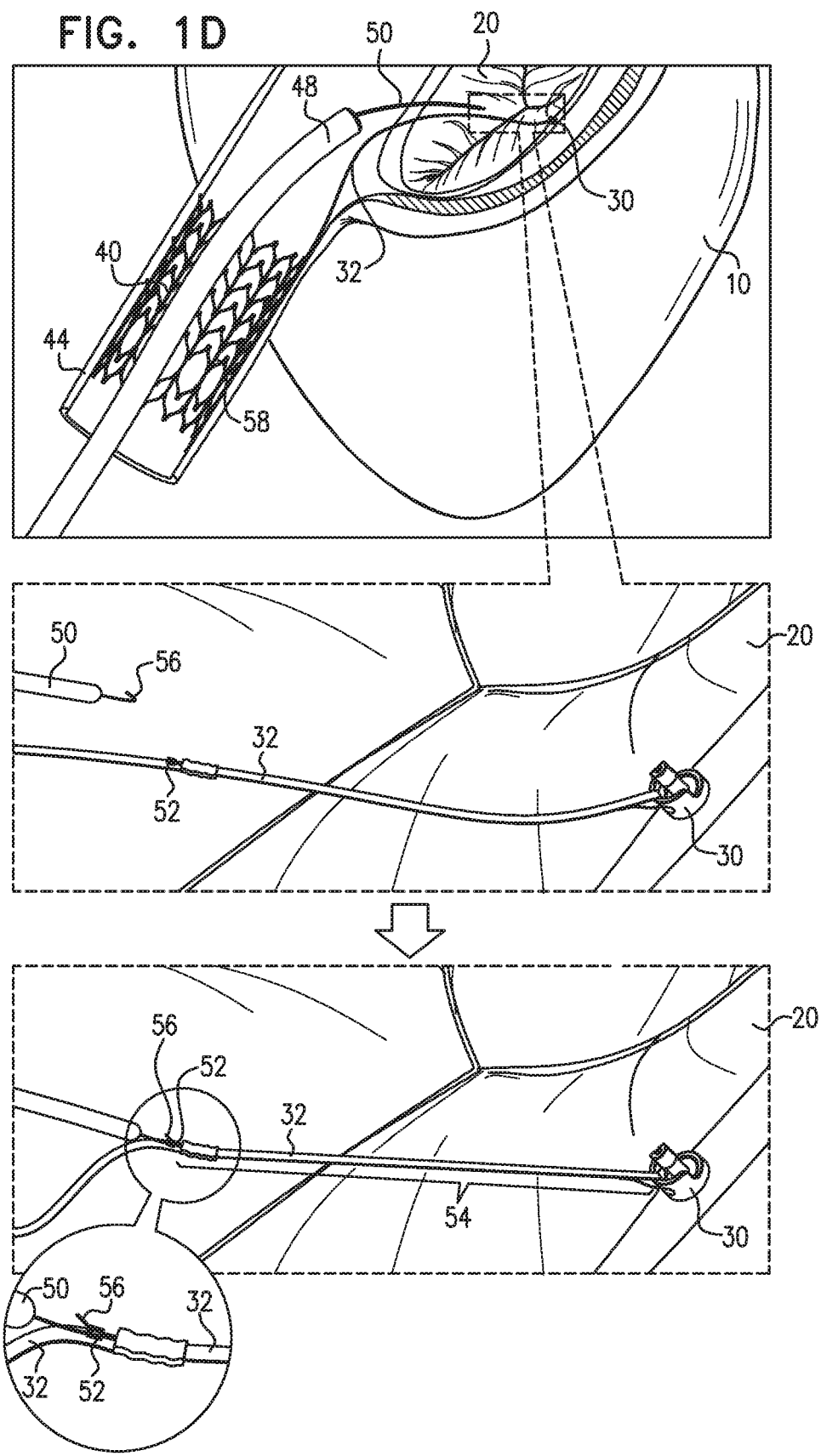
Figure 1E:
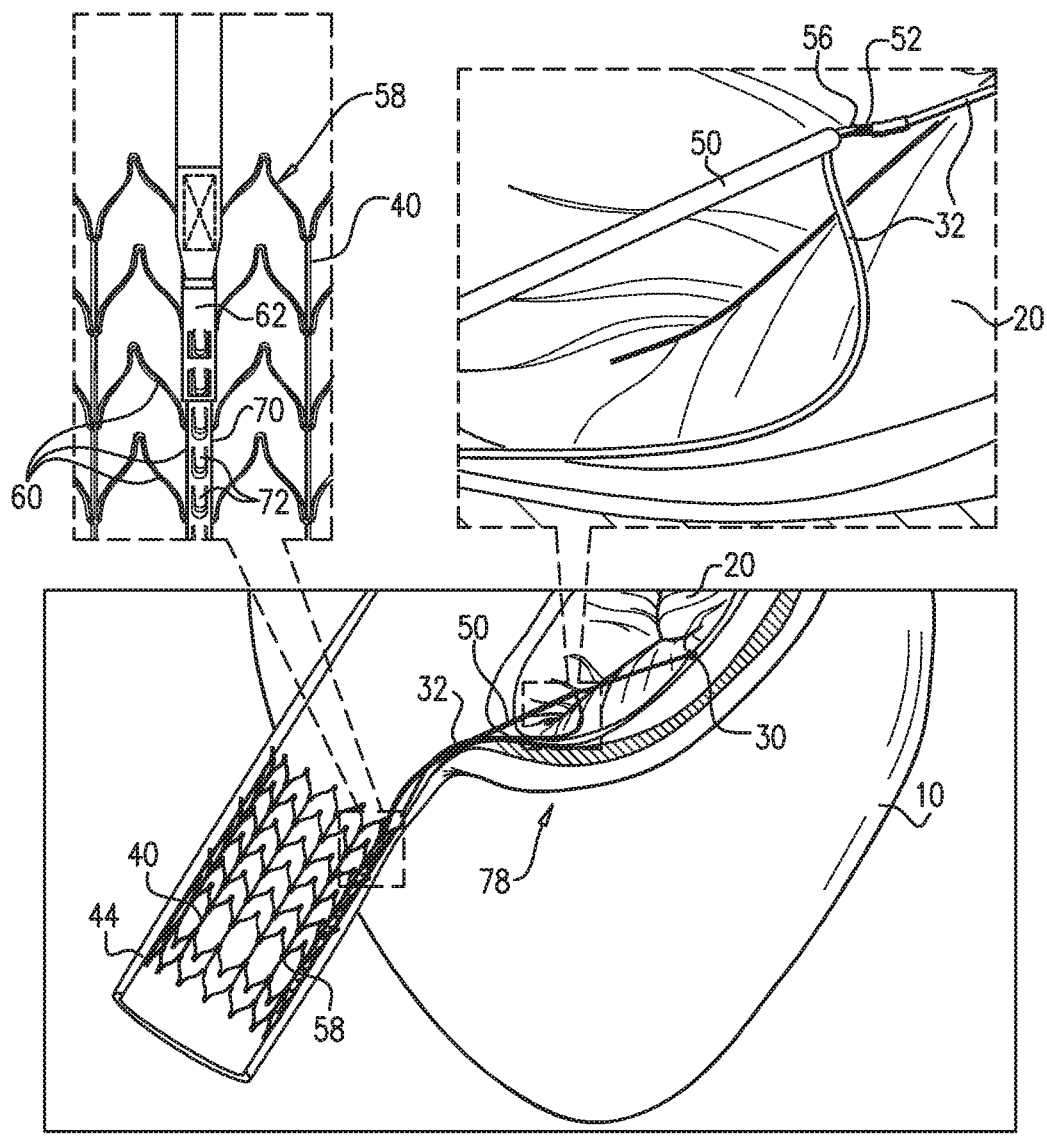

For some applications, coupling second tether 50 to coupling site 52 comprises coupling, to coupling site 52, a coupling element 56 that is attached to second tether 50. For example, coupling element 56 may comprise a hook, as shown in FIGS. 1D-E.

Typically, applying the tension comprises coupling second tether 50 to second tissue anchor 40. For some applications, as shown, second tissue anchor 40 comprises a stent 58 that comprises a plurality of struts 60, and coupling second tether 50 to second tissue anchor 40 comprises coupling, to one or more of struts 60, a coupling element 62 that is attached to second tether 50. For some applications, coupling element 62 is shaped so as to define an opening 64, e.g., exactly one opening 64 or a plurality of openings 64, arranged, for example, axially along coupling element 62. Optionally, opening 64 is defined by a loop of coupling element 62. Providing a plurality of openings 64 provides redundancy; in case one of the openings does not catch on stent 58, another of the openings may catch (or both may catch, as shown in the figures). Optionally, coupling element 62 comprises one or more loops that are shaped so as to define the one or more openings 64, respectively.

For some applications, at least one of struts 60 is oriented axially (i.e., along the axis of the stent) as a backbone 70 (which may be thicker, wider, and/or stronger than other struts 60 and/or other axially-oriented struts 60). Coupling element 62 is coupled to backbone 70. In one configuration, backbone 70 is shaped so as to define one or more hooks 72 (e.g., exactly one hook 72, or two or more hooks 72), and coupling element 62 is coupled to one or more of hooks 72. For example, coupling element 62 may be shaped so as to define one or more openings 64, as described above. Providing a plurality of hooks 72 provides redundancy, as discussed above regarding openings 64.

Alternatively, for some applications, coupling element 62 comprises one or more hooks, which are hooked onto one or more of struts 60, such as backbone 70. For example, coupling element 62 may comprise one of coupling elements 96A, 96B, 96C, and 96D, described hereinbelow with reference to FIGS. 3A-D.

Reference is made to FIG. 1E. For some applications, a system 78 for treating a heart of a patient is provided. System 78 comprises first and second tissue anchors 30 and 40, and the one or more first tethers 32 that couple together first and second tissue anchors 30 and 40. System 78 further comprises second tether 50, which is configured to be coupled to coupling site 52 along the one or more first tethers 32, so as to apply tension between first and second tissue anchors 30 and 40 using (a) second tether 50 and (b) longitudinal portion 54 of the one or more first tethers 32. (Longitudinal portion 54 typically extends from coupling site 52 to first tissue anchor 30.) For some applications, system 78 further comprises coupling element 56 that is attached to second tether 50 and is configured to be coupled to coupling site 52 along the one or more first tethers 32. System 78 may alternatively or additionally comprise any of the other elements and/or features described hereinabove with reference to FIGS. 1A-E.

For some applications, such as shown in FIGS. 2A-D, a longitudinal portion 80 of the one or more tethers 32 passes through one or more openings 82 of a locking frame 84 so as to form a tether loop 86. As shown in FIGS. 2B-D, the tension is applied by enlarging tether loop 86 by pulling on tether loop 86. For example, a hooking element 88 may be introduced, for example, through a catheter 48, and used to temporarily snag tether loop 86 and pull on the tether loop. (The catheter may be introduced through the same vena cava as during the first stage of the implantation procedure, or through the other vena cava.) A distal end 90 of catheter 48 may be held against locking frame 84 to provide a counter-force for pulling on the tether loop. For some applications, openings 82 are configured to provide sufficient friction to prevent tether loop 86 from contracting when ordinary tensions are applied to the one or more tethers 32. For some applications, such as shown in FIGS. 2A-D, the one or more openings 82 are two openings 82, and longitudinal portion 80 of the one or more tethers 32 passes through the two openings 82.

Reference is made to FIG. 2D. For some applications, a system 94 for treating a heart of a patient is provided. System 94 comprises first and second tissue anchors 30 and 40, and the one or more tethers 32 that couple together first and second tissue anchors 30 and 40. Longitudinal portion 80 of the one or more tethers 32 passes through the one or more openings 82 of locking frame 84 so as to form tether loop 86, such that enlargement of tether loop 86 by pulling on tether loop 86 applies tension between first and the second tissue anchors 30 and 40 using at least a longitudinal portion of the one or more tethers 32. System 94 may alternatively or additionally comprise any of the other elements and/or features described hereinabove with reference to FIGS. 2A-D.

Reference is again made to FIGS. 1A-E and is additionally made to FIGS. 3A-D, which are schematic illustrations of coupling elements 96A, 96B, 96C, and 96D, respectively, in accordance with respective applications of the present invention. For some applications, coupling element 56, described hereinabove with reference to FIGS. 1A-E, comprises one of coupling elements 96A, 96B, 96C, and 96D. Alternatively or additionally, for some applications in which coupling element 62 comprises one or more hooks, as described hereinabove with reference to FIGS. 1A-E, coupling element 62 comprises one of coupling elements 96A, 96B, 96C, and 96D.

Reference is now made to FIGS. 4A-D, FIGS. 5A-D, FIGS. 6A-B, FIGS. 7A-D, FIGS. 8A-D, and FIGS. 9A-B, which are schematic illustrations of respective techniques for treating heart 10 of a patient, in accordance with respective applications of the present invention. For some applications, these techniques are used to treat tricuspid valve 20, such as by reducing tricuspid valve regurgitation.

As shown in FIGS. 4A, 5A, 7A, and 8A, during a first stage of an implantation procedure, a first tissue anchor 130 is implanted in cardiac tissue of the patient. For example, first tissue anchor 130 may be implanted in the vicinity of tricuspid valve 20 (as shown), e.g., on or near the annulus. Typically, first tissue anchor 130 is implanted in a transcatheter procedure (typically endovascularly, such as percutaneously), via one or more catheters 48, such as described in the applications incorporated hereinbelow by reference. For some applications, first tissue anchor 130 comprises a helical tissue-anchoring element, or one of the anchors described in PCT Publications WO 2016/087934 and/or WO 2016/18939, which are incorporated herein by reference.

Upon completion of the first stage of the implantation procedure, first tissue anchor 130 has no beneficial effect by itself on the heart. For example, first tissue anchor 130 does not reshape the heart valve or reduce valve regurgitation by itself.

As shown in FIGS. 4B-D, 5B-D, 7B-D, and 8B-D, thereafter, during a second stage of the implantation procedure, typically after allowing at least 24 hours (e.g., at least one week, such as at least one month) for tissue growth (e.g., fibrous and/or endothelial tissue growth) on first tissue anchor 130 to strengthen anchoring of first tissue anchor 130 in the cardiac tissue:

a second tissue anchor 140 is implanted in the patient;
  first and second tissue anchors 130 and 140 are coupled together using one or more tethers 132, as shown in FIGS. 4B, 5B-C, 6A-B, 7B-C, 9A-B, and 8B-C; and
  tension is applied between first and second tissue anchors 130 and 140 using the one or more tethers 132, as shown in FIGS. 4C-D, 5D, 7D, and 8D.

First and second tissue anchors 130 and 140 may be coupled together either after or before implanting second tissue anchor 140. For some applications, second tissue anchor 140 is implanted in superior vena cava (SVC) 42, inferior vena cava (IVC) 44 (as shown), or coronary sinus 46. Typically, second tissue anchor 140 is implanted in a transcatheter procedure (typically endovascularly, such as percutaneously), via one or more catheters 48, such as described in the applications incorporated hereinbelow by reference. For some applications, second tissue anchor 140 is implanted within two months after implanting first tissue anchor 130. (The catheter used during the second stage of the implantation procedure may be introduced through the same vena cava as during the first stage of the implantation procedure, or through the other vena cava.)

For some applications, the one or more tethers 132 are fixed to second tissue anchor 140 before second tissue anchor 140 is introduced into the patient's body, while for other applications, the one or more tethers 132 are coupled to second tissue anchor 140 during the second stage of the implantation procedure, such as using techniques described hereinabove with reference to FIGS. 1A-E, 2A-D, and/or 3A-D. For some applications, second tissue anchor 140 comprises a stent 158. Stent 158 may implement any of the features of stent 58, described hereinabove with reference to FIGS. 1A-E and/or 2A-D.

Optionally, the one or more tethers 32 comprise two tethers 32 that are coupled together in situ during the second stage of the implantation procedure, such as using techniques described in one or more of the applications incorporated by reference hereinbelow.

For some applications, as shown in FIGS. 4B-D, 5B-D, 6A-B, 7B-D, 9A-B, and 8B-D, first tissue anchor 130 comprises a tissue-anchoring element 142 and a first coupling element 144. The one or more tethers 132 are attached to second tissue anchor 140 and comprise a second coupling element 146. First and second tissue anchors 130 and 140 are coupled together using the one or more tethers 132 by coupling second coupling element 146 to first coupling element 144. Optionally, first coupling element 144 is coated with a tissue-growth-inhibiting coating, e.g., silicone, and/or tissue-anchoring element 142 is coated with a tissue-growth-enhancing coating.

Reference is made to FIG. 4A-D. For some applications, second coupling element 146 comprises a loop 160, and first and second tissue anchors 130 and 140 are coupled together by coupling loop 160 to first coupling element 144. For example, first coupling element 144 may comprise a hook 162, to which loop 160 is coupled. Hook 162 may have various shapes, such as a bowl (as shown), a disc, a hook similar to hook 72 (shown in FIG. 1D), or coupling elements 96A, 96B, 96C, and 96D (shown in FIGS. 3A-D, respectively).

Figure 4A:
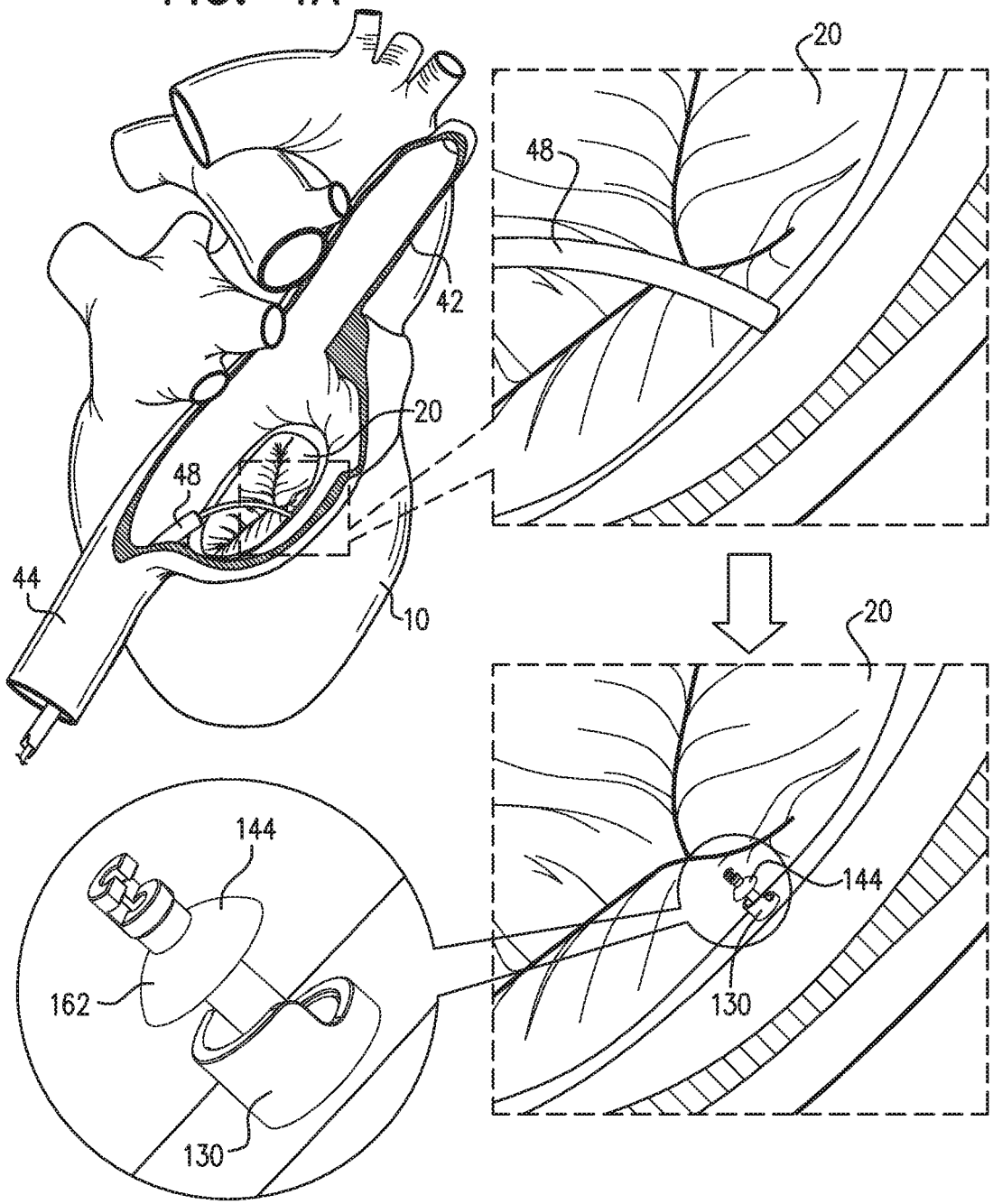
FIGS. 4A-D are schematic illustrations of a technique for treating a heart of a patient, in accordance with respective applications of the present invention.
Figure 4B:
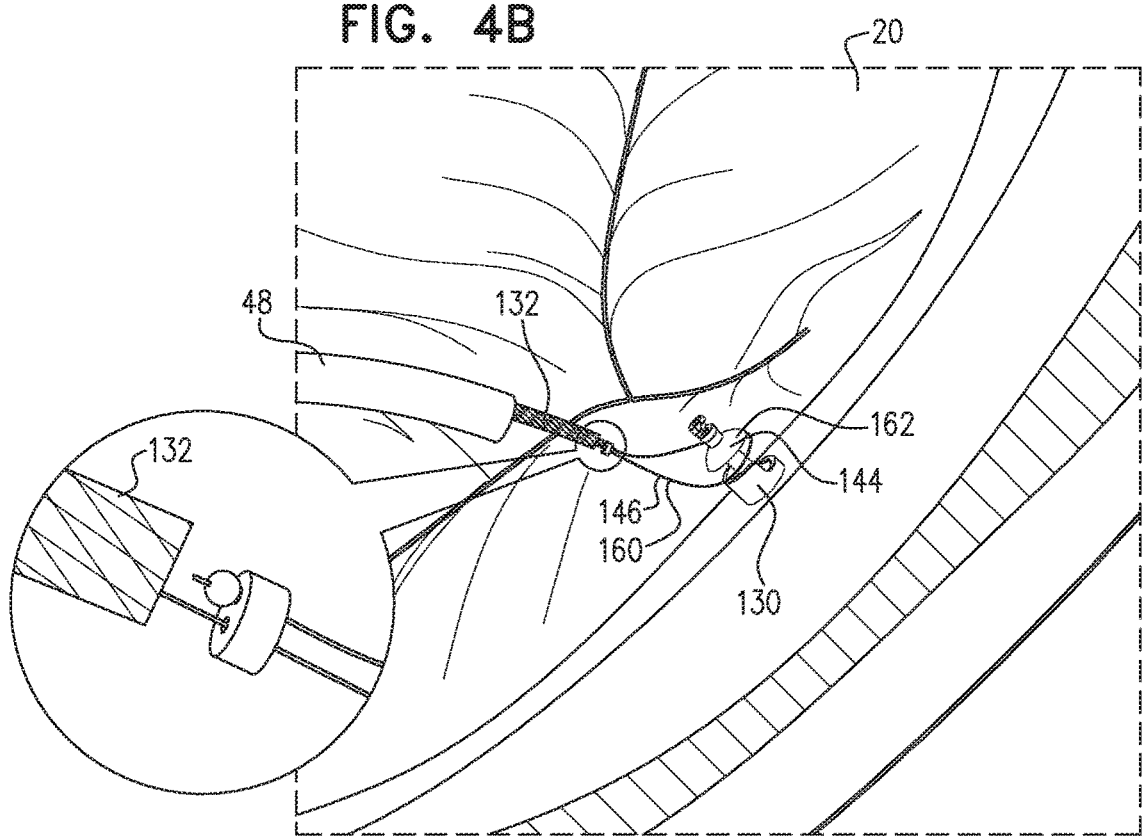
Figure 4C:
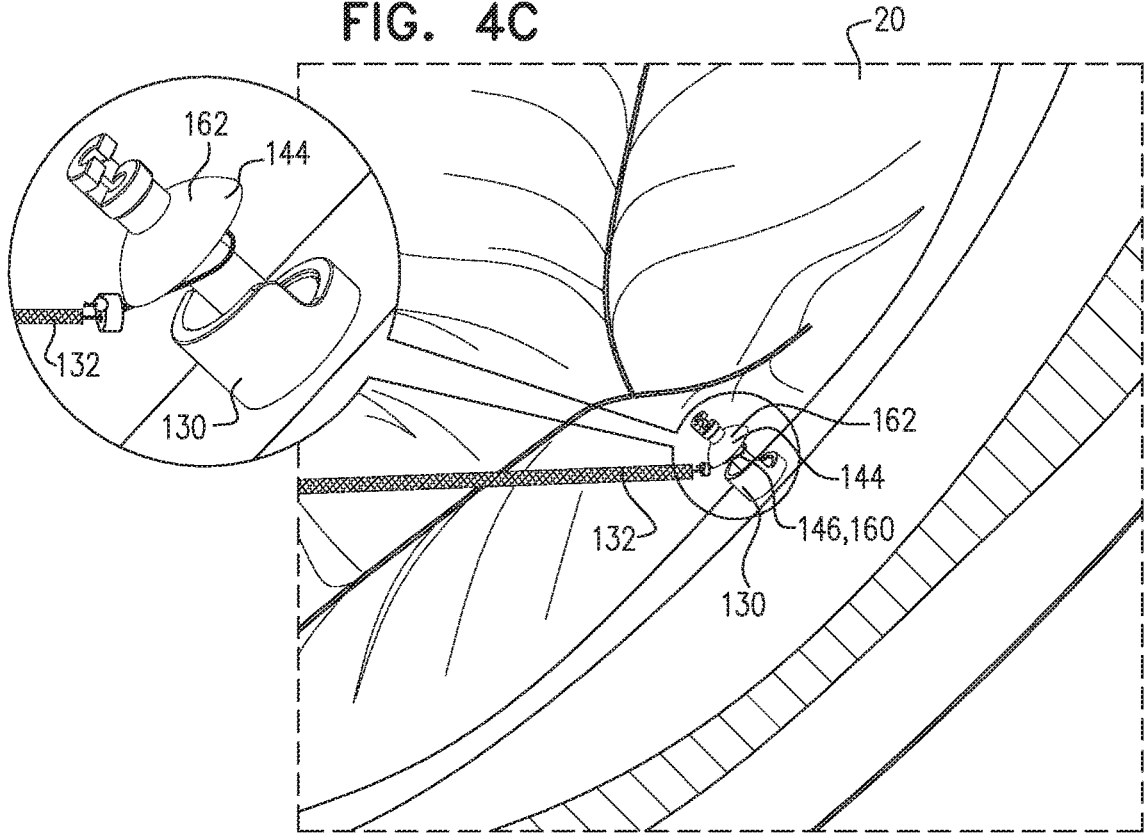
Figure 4D:
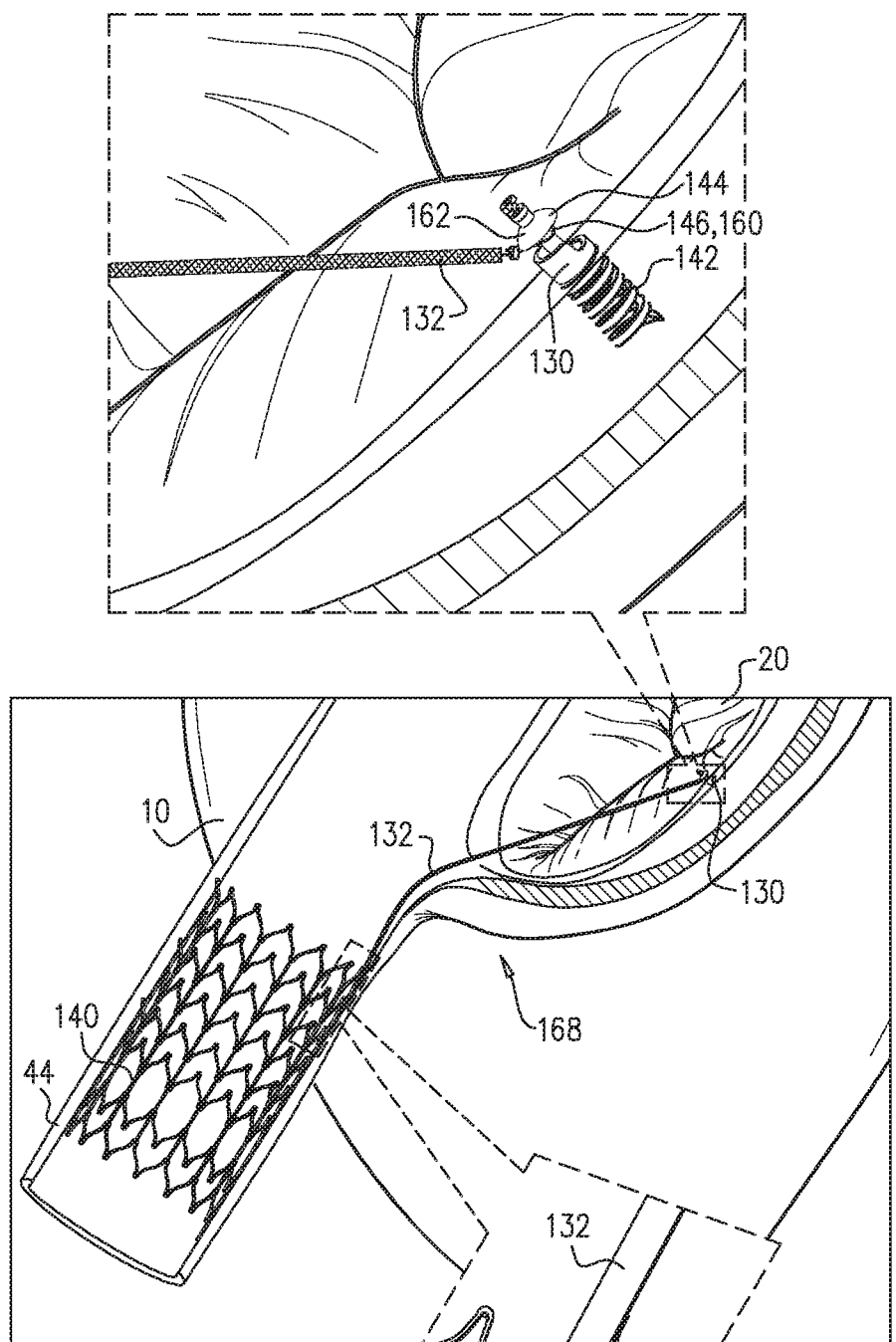

Reference is made to FIG. 4D. For some applications, a system 168 for treating a heart of a patient is provided. System 168 comprises:
first tissue anchor 130, which is configured to be implanted in cardiac tissue of the patient, and which comprises tissue-anchoring element 142 and first coupling element 144 that comprises hook 162,
second tissue anchor 140, which is configured to be implanted in the patient, and
the one or more tethers 132, which are attached to second tissue anchor 140 and comprise second coupling element 146, which comprises loop 160, and which is configured to be coupled to first coupling element 144 by looping loop 160 onto hook 162.

System 168 may alternatively or additionally comprise any of the other elements and/or features described hereinabove with reference to FIGS. 4A-D.

Reference is now made to FIGS. 5A-D and 6A-B. For some applications, first coupling element 144 comprises a loop 164, and second coupling element 146 comprises a hook 166. First and second tissue anchors 130 and 140 are coupled together by hooking hook 166 onto loop 164.

Figure 5A:
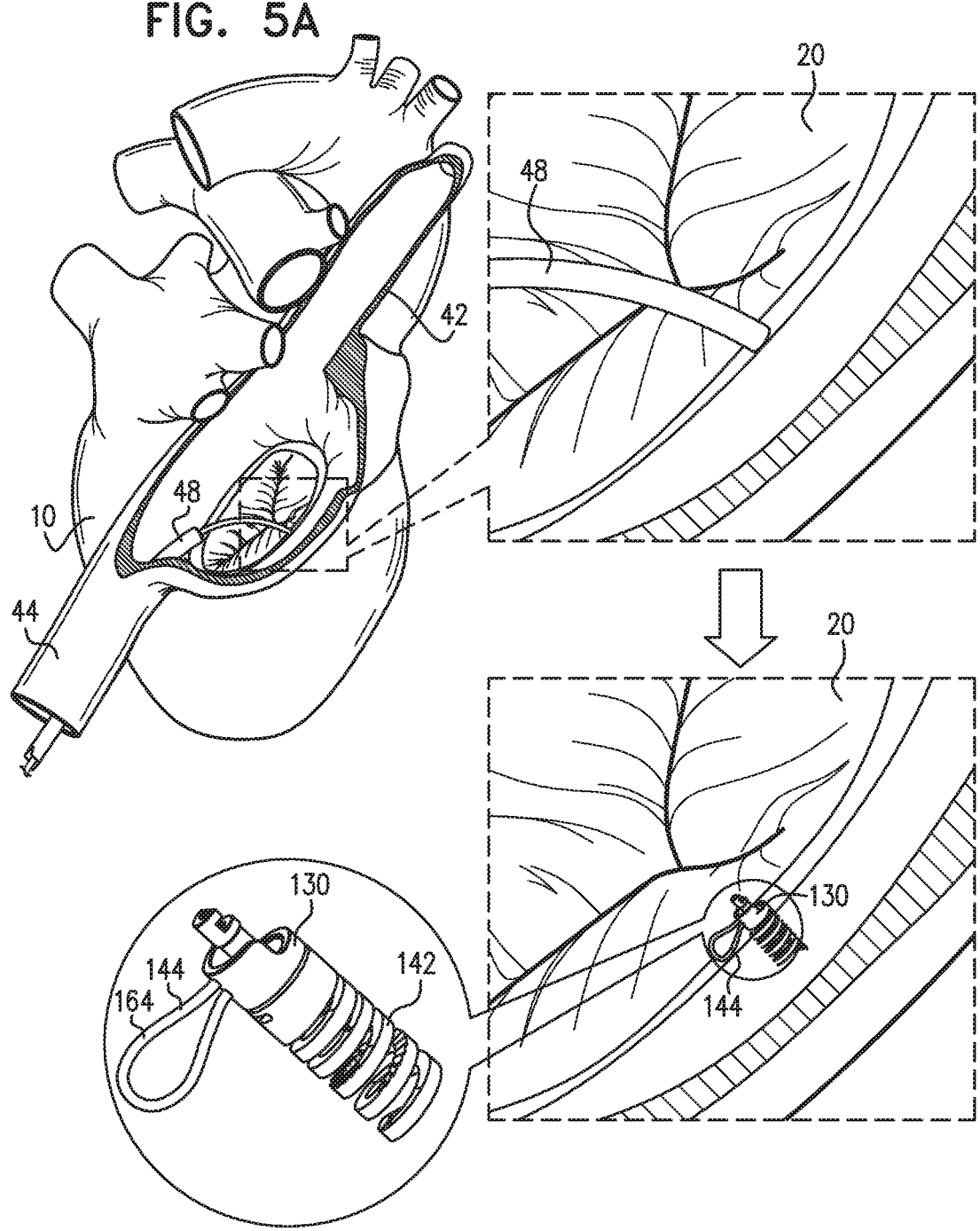
FIGS. 5A-D are schematic illustrations of another technique for treating a heart of a patient, in accordance with respective applications of the present invention.
Figure 5B:
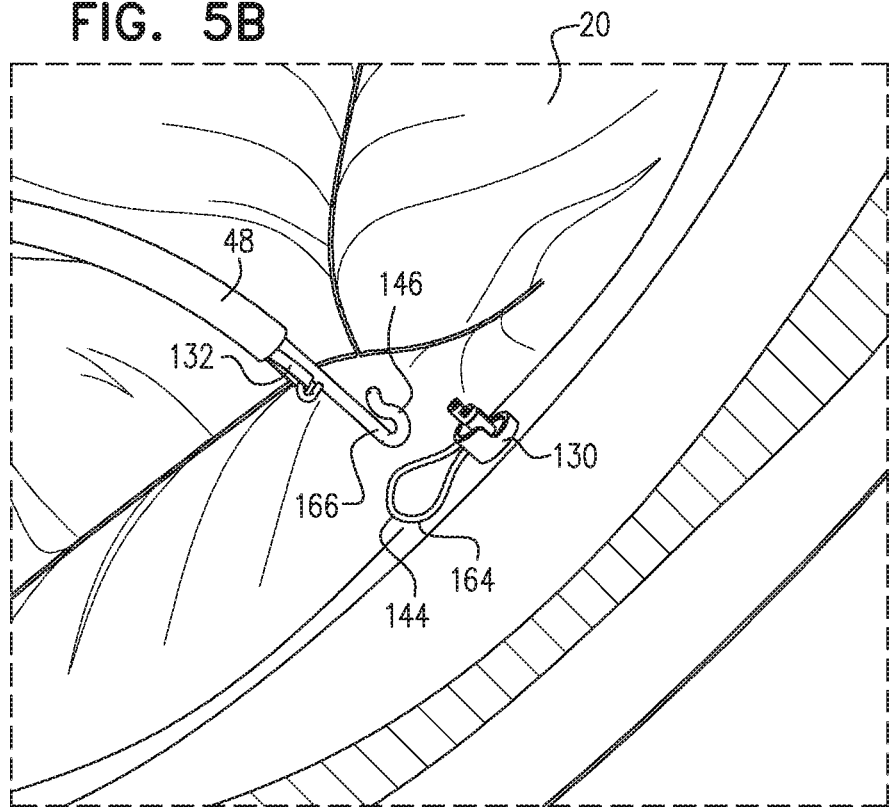
Figure 5C:
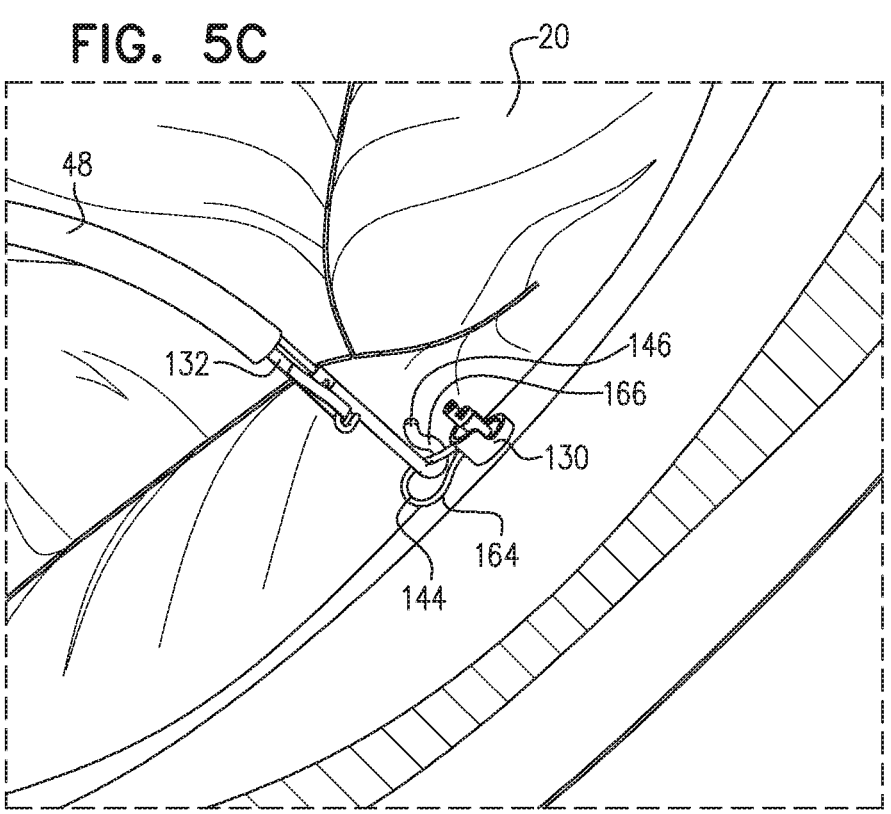
Figure 5D:
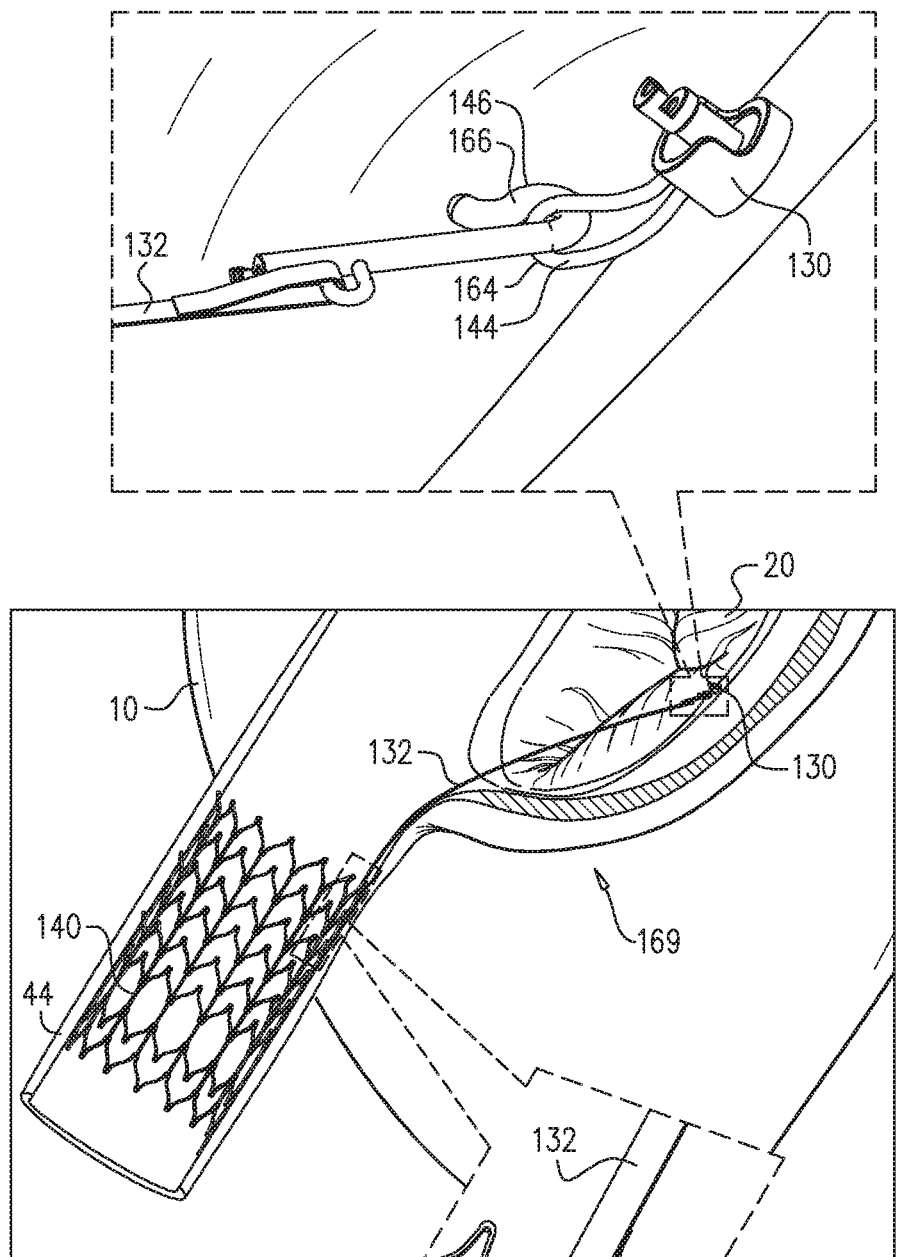
Figure 6A:
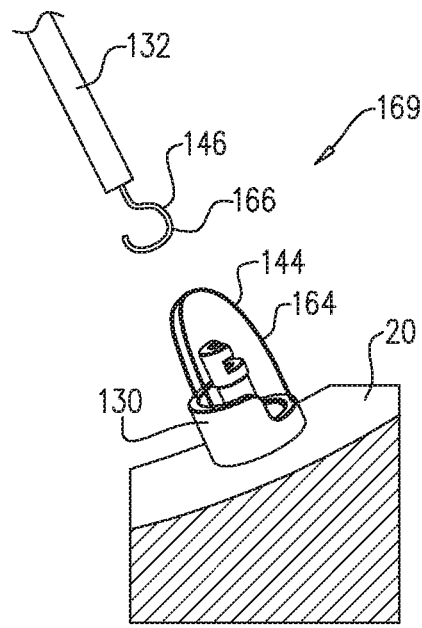
FIGS. 6A-B are schematic illustrations of a yet another technique for treating a heart of a patient, in accordance with respective applications of the present invention.
Figure 6B:
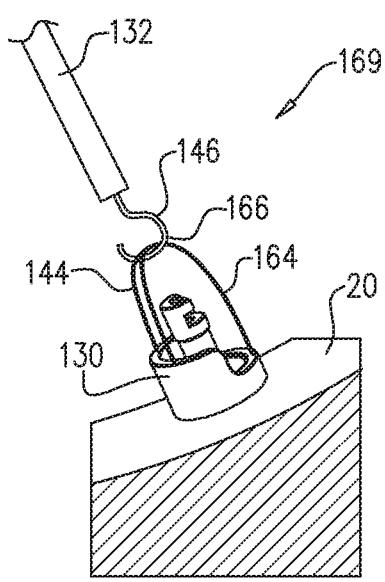

Reference is made to FIGS. 5D and 6A-B. For some applications, a system 169 for treating a heart of a patient is provided. System 169 comprises:
first tissue anchor 130, which is configured to be implanted in cardiac tissue of the patient, and which comprises tissue-anchoring element 142 and first coupling element 144 that comprises loop 164,
second tissue anchor 140, which is configured to be implanted in the patient, and
the one or more tethers 132, which are attached to second tissue anchor 140 and comprise second coupling element 146, which comprises hook 166, and which is configured to be coupled to first coupling element 144 by hooking hook 166 onto loop 164.

System 169 may alternatively or additionally comprise any of the other elements and/or features described hereinabove with reference to FIGS. 5A-D and/or 6A-B.

Reference is now made to FIGS. 7A-D and 8A-D. For some applications, first coupling element 144 comprises a ball 170, and second coupling element 146 comprises a socket 172. First and second tissue anchors 130 and 140 are coupled together by coupling socket 172 to ball 170. Optionally, ball 170 is connected to a head 174 of first tissue anchor 130 by a rod 176.

Figure 8A:
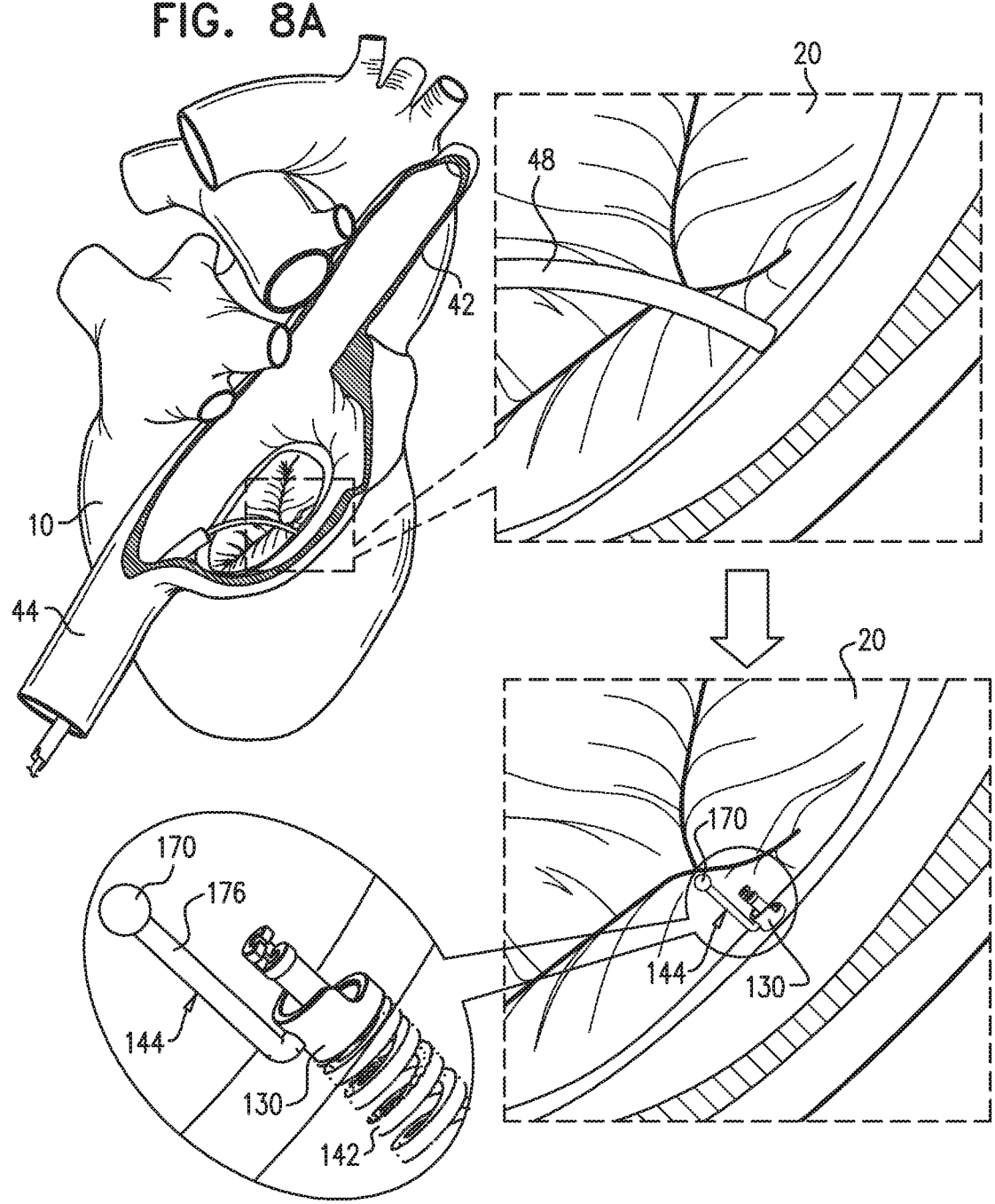
FIGS. 8A-D are schematic illustrations of an additional technique for treating a heart of a patient, in accordance with respective applications of the present invention.
Figure 8B:
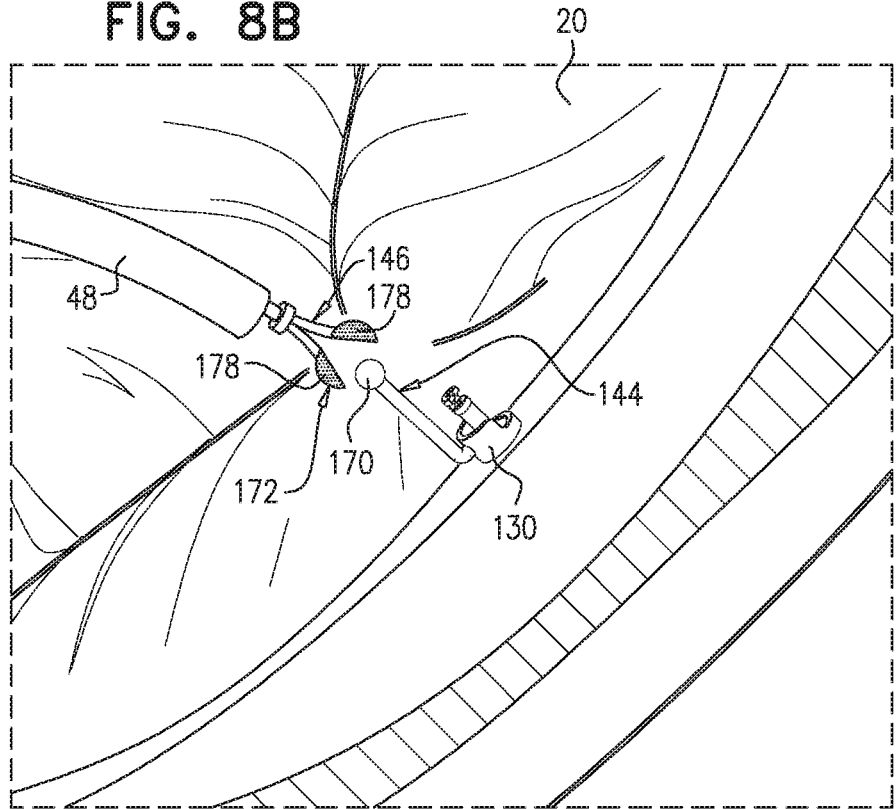
Figure 8C:
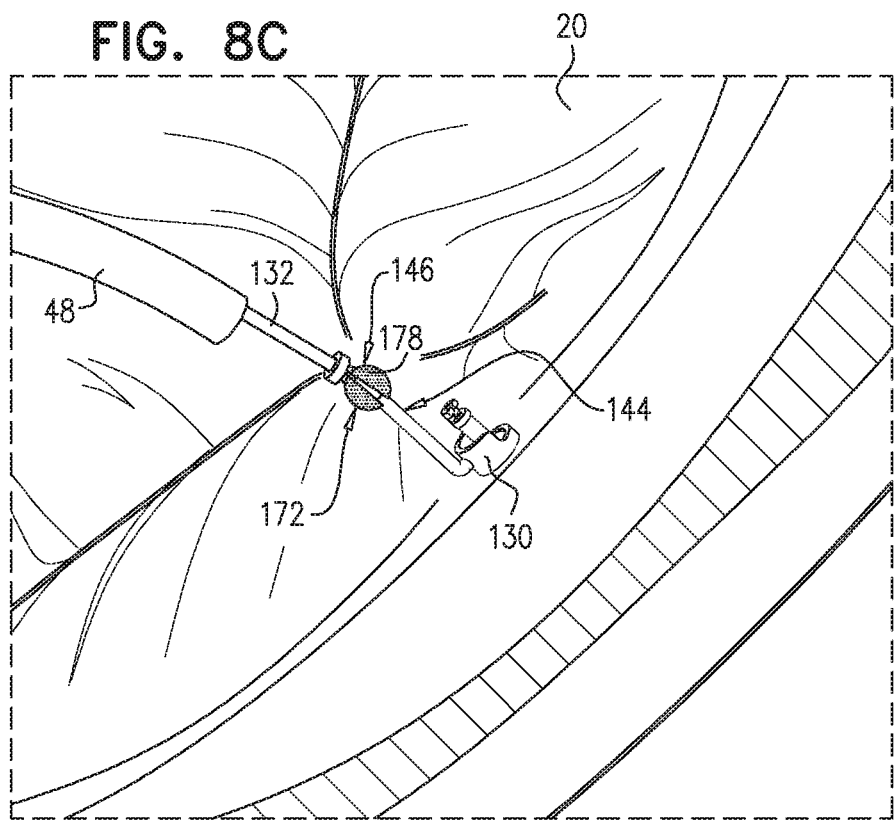
Figure 8D:
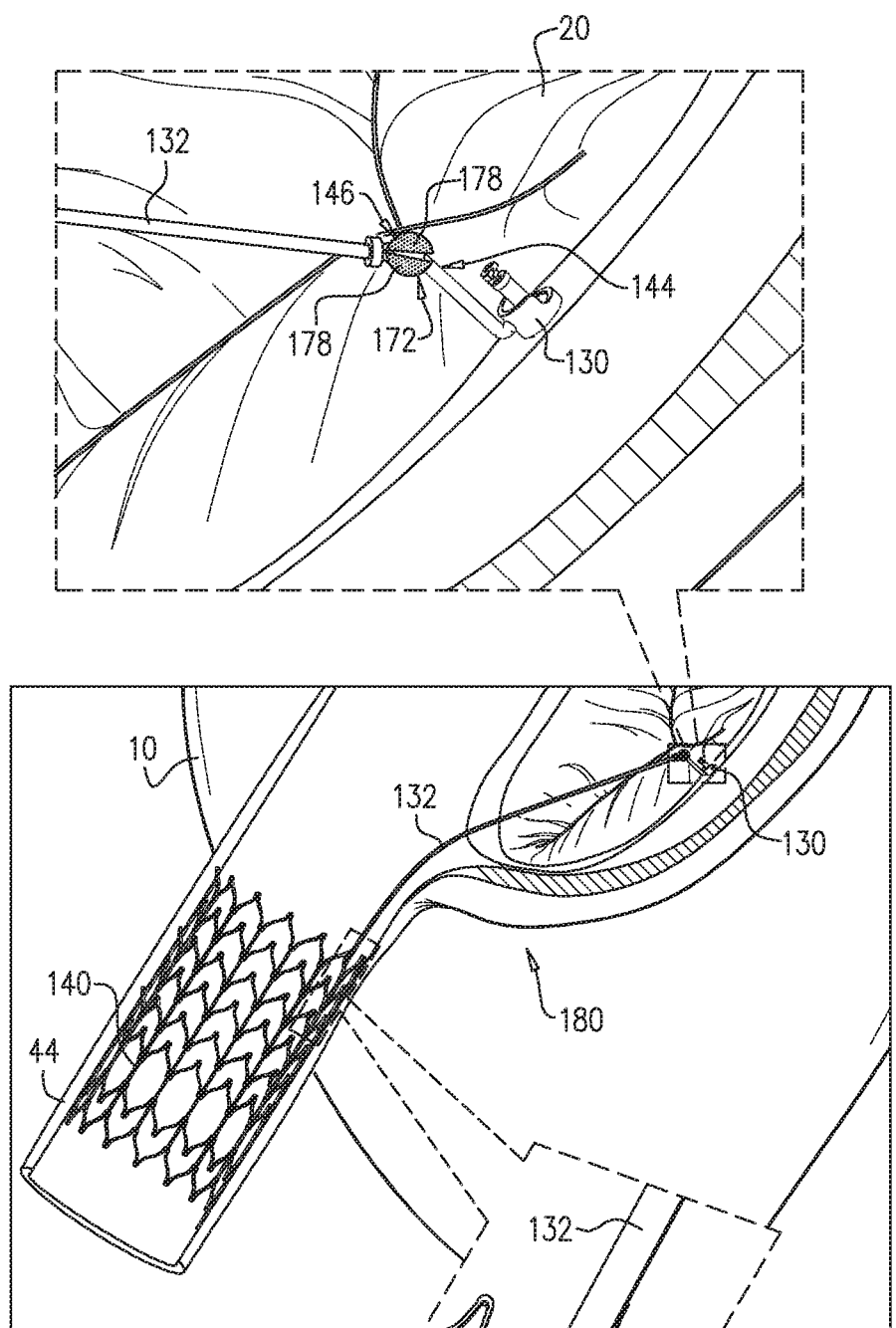

For some applications, such as shown in FIGS. 8A-D, coupling socket 172 to ball 170 comprises transitioning socket 172 from an open, unlocked state, such as shown in FIG. 8B, to a closed, locked state around ball 170, such as shown in FIGS. 8C-D. For example, socket 172 may comprise two gripping elements 178 (e.g., which are generally semispherical), which are at least partially separate from each other in the open, unlocked state and brought toward each other in the closed, locked state.

Figure 7A:
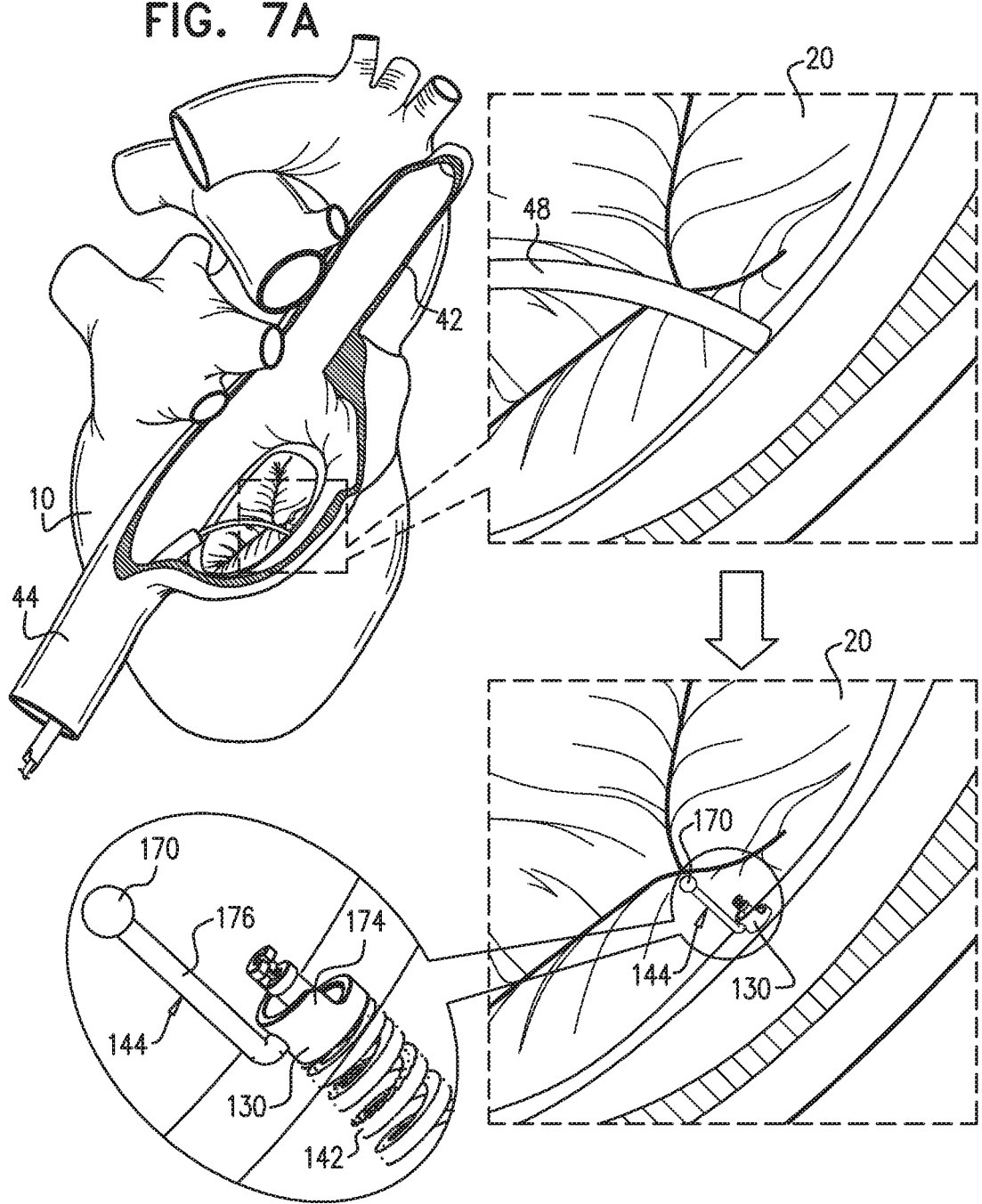
FIGS. 7A-D are schematic illustrations of a further technique for treating a heart of a patient, in accordance with respective applications of the present invention.
Figure 7B:
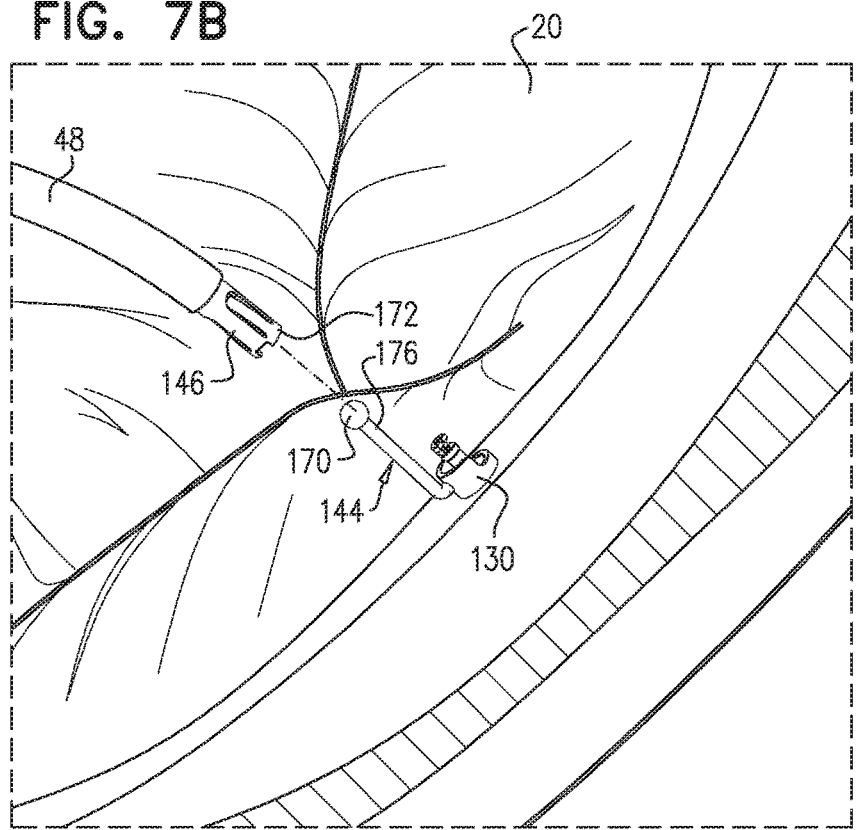
Figure 7C:
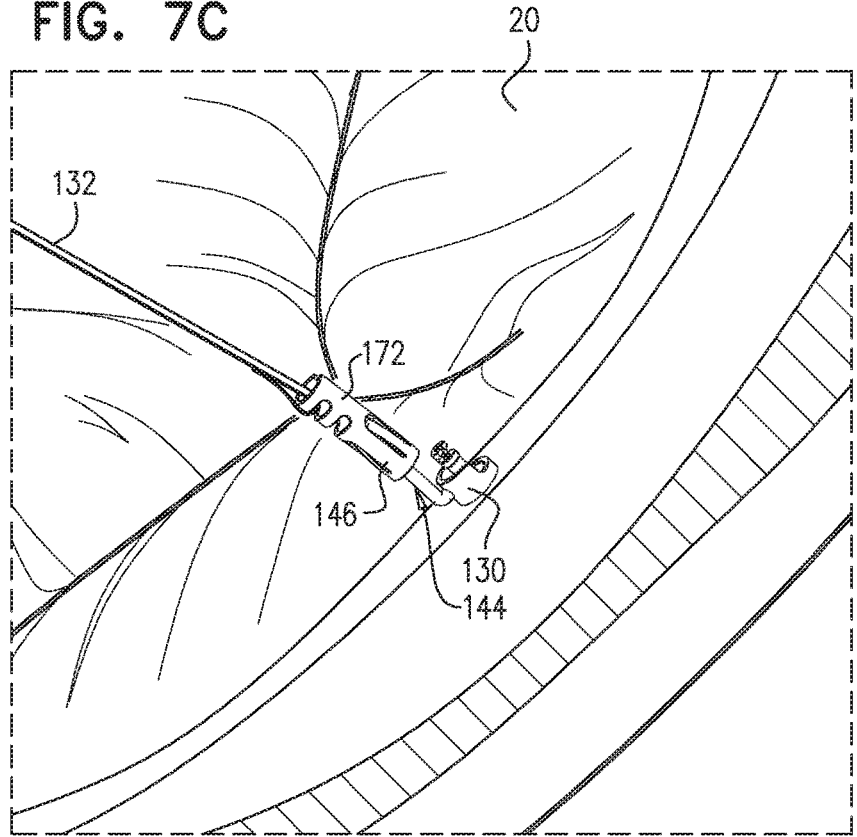
Figure 7D:
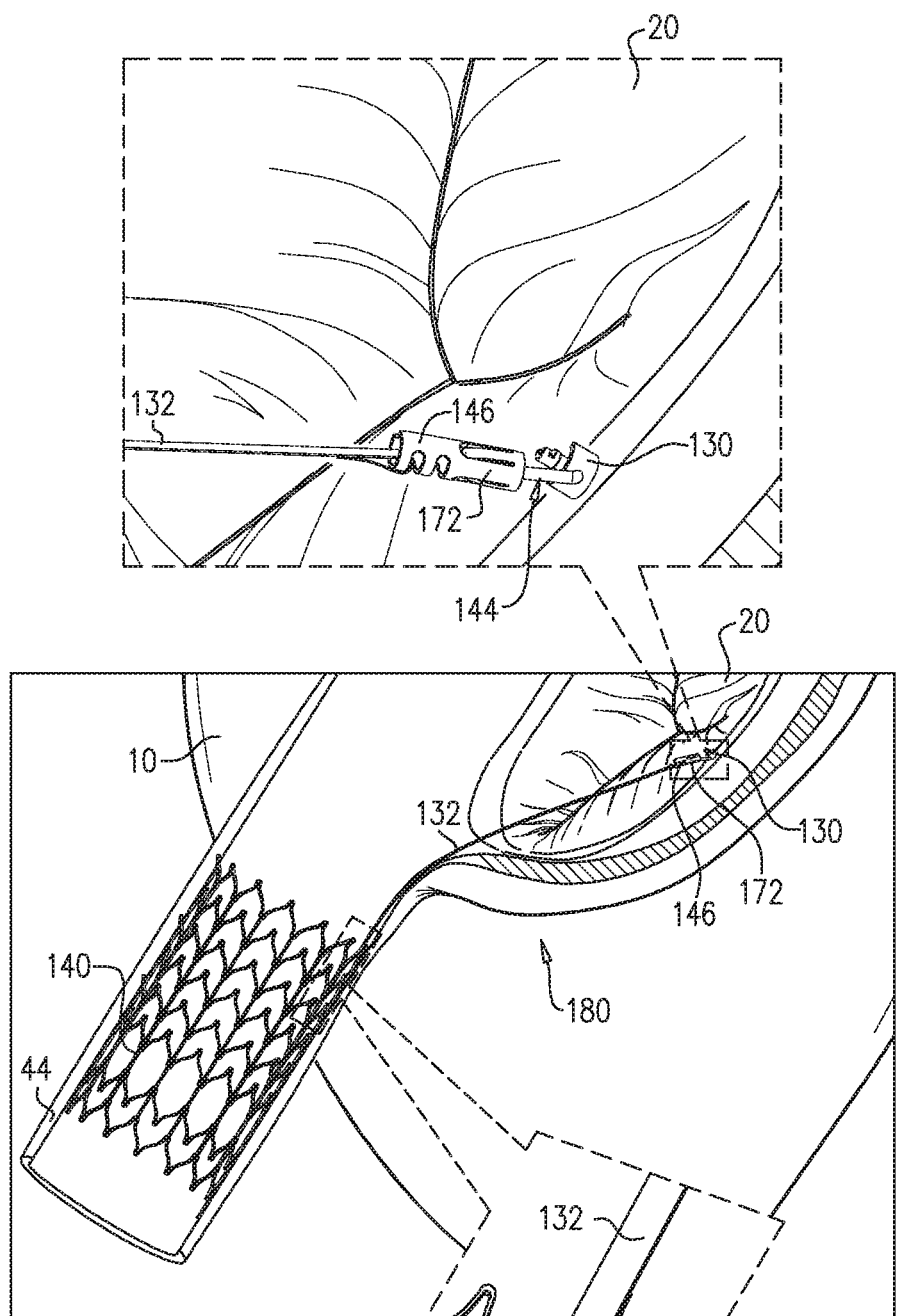

Reference is made to FIGS. 7D and 8D. For some applications, a system 180 for treating a heart of a patient is provided. System 180 comprises:
first tissue anchor 130, which is configured to be implanted in cardiac tissue of the patient, and which comprises tissue-anchoring element 142 and first coupling element 144 that comprises ball 170,
second tissue anchor 140, which is configured to be implanted in the patient, and
the one or more tethers 132, which are attached to second tissue anchor 140 and comprise second coupling element 146, which comprises socket 172, and which is configured to be coupled to first coupling element 144 by coupling socket 172 to ball 170.

System 180 may alternatively or additionally comprise any of the other elements and/or features described hereinabove with reference to FIGS. 7A-D and 8A-D.

Figure 9A:
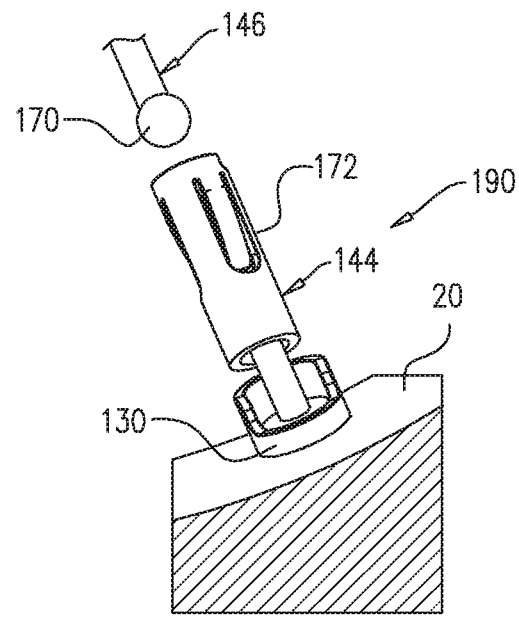
FIGS. 9A-B are schematic illustrations of yet another technique for treating a heart of a patient, in accordance with respective applications of the present invention.
Figure 9B:
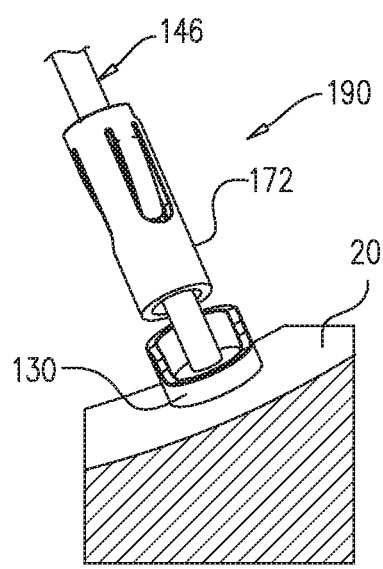

Reference is made to FIGS. 9A-B. For some applications, first coupling element 144 comprises socket 172, and second coupling element 146 comprises ball 170. First and second tissue anchors 130 and 140 are coupled together by coupling ball 170 to socket 172.

Reference is still made to FIGS. 9A-B. For some applications, a system 190 for treating a heart of a patient is provided. System 180 comprises:
first tissue anchor 130, which is configured to be implanted in cardiac tissue of the patient, and which comprises tissue-anchoring element 142 and first coupling element 144 that comprises socket 172,
second tissue anchor 140, which is configured to be implanted in the patient, and
the one or more tethers 132, which are attached to second tissue anchor 140 and comprise second coupling element 146, which comprises ball 170, and which is configured to be coupled to first coupling element 144 by coupling ball 170 to socket 172.

System 190 may alternatively or additionally comprise any of the other elements and/or features described hereinabove with reference to FIGS. 9A-B.

Reference is now made to FIGS. 10A-D, which are schematic illustrations of a technique for treating heart 10 of a patient, in accordance with an application of the present invention. For some applications, this technique is used to treat tricuspid valve 20, such as by reducing tricuspid valve regurgitation. The technique of FIGS. 10A-D may be practiced in combination with any of the features described hereinabove with reference to FIGS. 4A-D, 5A-D, 6A-B, 7A-D, 8A-D, and/or 9A-B, mutatis mutandis. In this configuration, the one or more tethers 132 are one or more first tethers 132.

Figure 10A:
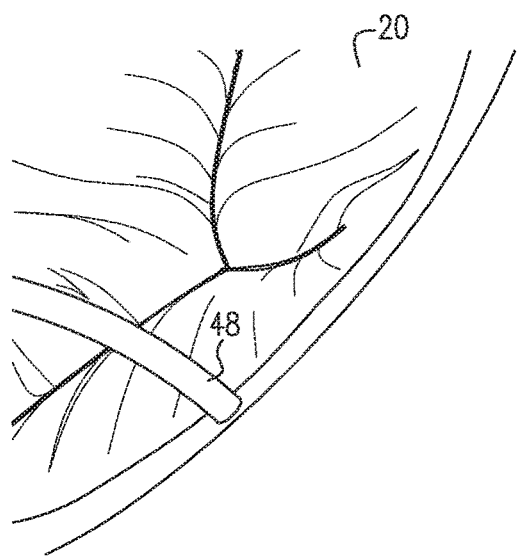
FIGS. 10A-D are schematic illustrations of a further technique for treating a heart of a patient, in accordance with respective applications of the present invention.
Figure 10B:
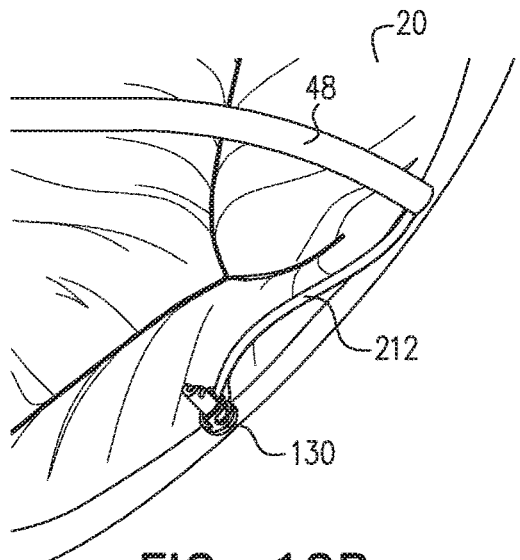
Figure 10C:
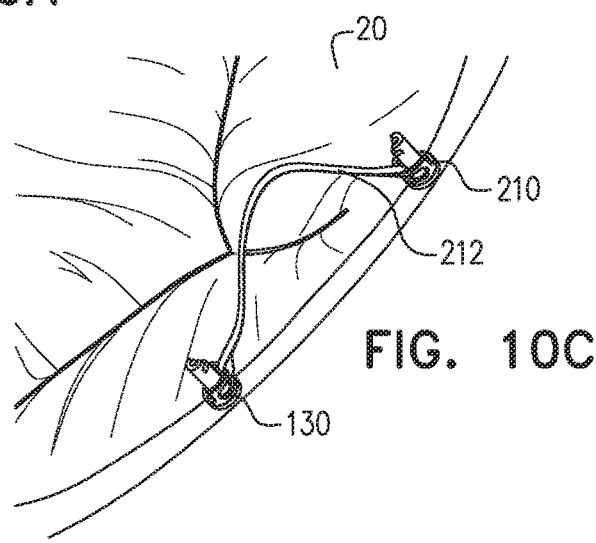

In addition to implanting first tissue anchor 130, such as described hereinabove with reference to FIGS. 4A-D, 5A-D, 6A-B, 7A-D, 8A-D, and 9A-B, and shown in FIG. 10A, during the first stage of the implantation procedure, typically within three hours of implanting first tissue anchor 130, a third tissue anchor 210 is implanted in cardiac tissue of the patient, such that first and third tissue anchors 130 and 210 are coupled together by one or more second tethers 212 (e.g., exactly one second tether 212), as shown in FIGS. 8B-C. For example, third tissue anchor 210 may be implanted in the vicinity of tricuspid valve 20 (as shown), e.g., on or near the annulus. Optionally, the one or more second tethers 212 comprise two second tethers 212 that are coupled together in situ during the first stage of the implantation procedure, such as using techniques described in one or more of the applications incorporated by reference hereinbelow. (The catheter used during the second stage of the implantation procedure may be introduced through the same vena cava as during the first stage of the implantation procedure, or through the other vena cava.)

First and second tissue anchors 130 and 140 are coupled together by coupling first, second, and third tissue anchors 130, 140, and 210 together using the one or more first tethers 132 and the one or more second tethers 212. The tension is applied between first and second tissue anchors 130 and 140 by applying the tension between first, second, and third tissue anchors 130, 140, and 210 using the one or more first tethers 132 and the one or more second tethers 212.

For some applications, the one or more first tethers 132 are attached to second tissue anchor 140 (typically before introducing second tissue anchor 140 into the patient's body) and comprise a coupling element 146. First, second, and third tissue anchors 130, 140, and 210 are coupled together by coupling coupling element 146 to the one or more second tethers 212. For some applications, coupling element 146 comprises a hook 214, and coupling element 146 is coupled to the one or more second tethers 212 by hooking hook 214 onto the one or more second tethers 212. Optionally, coupling element 146 may comprise one of coupling elements 96A, 96B, 96C, and 96D, described hereinabove with reference to FIGS. 3A-D.

Figure 10D:
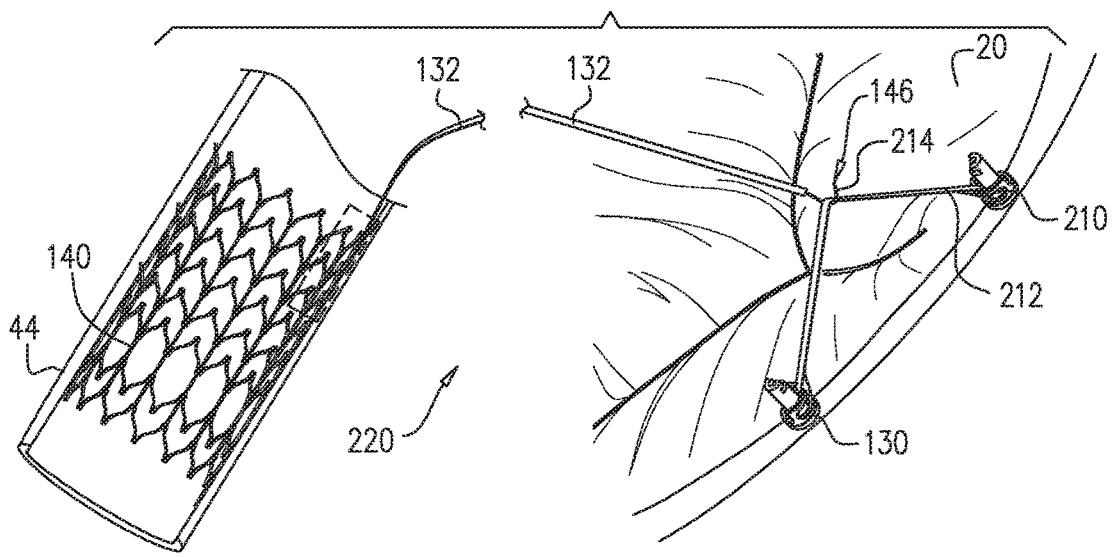

Reference is made to FIG. 10D. For some applications, a system 220 for treating a heart of a patient is provided. System 220 comprises:
- first and third tissue anchors 130 and 210 configured to be implanted in cardiac tissue of the patient,
- second tissue anchor 140 configured to be implanted in the patient,
- the one or more first tethers 132, which are attached to second tissue anchor 140 and comprise coupling element 146, and
- the one or more second tethers 212 that couple together first and third tissue anchors 130 and 210.

Coupling element 146 is configured to be coupled to the one or more second tethers 212, to facilitate applying tension between first, second, and third tissue anchors 130, 140, and 210 using the one or more first tethers 132 and the one or more second tethers 212. System 220 may alternatively or additionally comprise any of the other elements and/or features described hereinabove with reference to FIGS. 10A-D, and/or with reference to FIGS. 4A-D, 5A-D, 6A-B, 7A-D, 8A-D, and/or 9A-B.

For some applications, fibrous glue is applied to the tissue-coupling elements of the tissue anchors described herein to help secure the anchors in place and minimize detachment. Optionally, tissue-growth-enhancing coating is also applied to the tissue-coupling elements, as described hereinabove.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 8,475,525 to Maisano et al.;
U.S. Pat. No. 8,961,596 to Maisano et al.;
U.S. Pat. No. 8,961,594 to Maisano et al.;
PCT Publication WO 2011/089601;
U.S. Pat. No. 9,241,702 to Maisano et al.;
PCT Publication WO 2013/011502;
U.S. Provisional Application 61/750,427, filed Jan. 9, 2013;
U.S. Provisional Application 61/783,224, filed Mar. 14, 2013;
PCT Publication WO 2013/179295;
U.S. Provisional Application 61/897,491, filed Oct. 30, 2013;
U.S. Provisional Application 61/897,509, filed Oct. 30, 2013;
U.S. Pat. No. 9,307,980 to Gilmore et al.;
PCT Publication WO 2014/108903;
PCT Publication WO 2014/141239;
U.S. Provisional Application 62/014,397, filed Jun. 19, 2014;
PCT Publication WO 2015/063580;
US Patent Application Publication 2015/0119936;
U.S. Provisional Application 62/086,269, filed Dec. 2, 2014;
U.S. Provisional Application 62/131,636, filed Mar. 11, 2015;
U.S. Provisional Application 62/167,660, filed May 28, 2015;
PCT Publication WO 2015/193728;
PCT Publication WO 2016/087934;
US Patent Application Publication 2016/0242762;
PCT Publication WO 2016/189391;
US Patent Application Publication 2016/0262741; and
U.S. Provisional Application 62/376,685, filed Aug. 18, 2016.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of treating a heart of a patient, comprising:
   implanting a first tissue anchor in cardiac tissue of the patient and a second tissue anchor in the patient, such that the first and the second tissue anchors are coupled together by one or more first tethers; and
   thereafter, after allowing at least 24 hours for tissue growth on the first tissue anchor to strengthen anchoring of the first tissue anchor in the cardiac tissue:
      coupling a second tether to a coupling site along the one or more first tethers; and
      applying tension between the first and the second tissue anchors using at least a longitudinal portion of the one or more first tethers and the second tether,
   wherein applying the tension comprises coupling the second tether to the second tissue anchor.

2. The method according to claim 1, wherein the one or more first tethers are slack before applying the tension.

3. The method according to claim 1, wherein coupling the second tether to the coupling site comprises coupling, to the coupling site, a coupling-site coupler that is attached to the second tether.

4. The method according to claim 3, wherein the coupling-site coupler comprises a hook.

5. The method according to claim 1, wherein the second tissue anchor comprises a stent that comprises a plurality of struts, and wherein coupling the second tether to the second tissue anchor comprises coupling, to one or more of the struts, a second-tissue-anchor element that is attached to the second tether.

6. The method according to claim 5, wherein the second-tissue-anchor coupler comprises a hook.

7. The method according to claim 5, wherein the second-tissue-anchor coupler is shaped so as to define an opening.

8. The method according to claim 5, wherein at least one of the struts is oriented axially as a backbone, and wherein coupling the second-tissue-anchor coupler to the one or more of the struts comprises coupling the second-tissue-anchor coupler to the backbone.

9. The method according to claim 8, wherein the backbone is shaped so as to define one or more hooks, and wherein coupling the second-tissue-anchor coupler to the backbone comprises coupling the second-tissue-anchor coupler to one or more of the hooks.

10. The method according to claim 1, wherein applying the tension comprises applying the tension after allowing at least one week for tissue growth on the first tissue anchor.

11. The method according to claim 1, wherein applying the tension comprises applying the tension within two months after implanting the first tissue anchor.

12. The method according to claim 1, wherein implanting the first tissue anchor comprises implanting the first tissue anchor in a vicinity of a tricuspid valve of the patient.

13. The method according to claim 1, wherein implanting the second tissue anchor comprises implanting the second tissue anchor in a blood vessel selected from the group consisting of: a superior vena cava (SVC), an inferior vena cava (IVC), and a coronary sinus.

* * * * *